(12) United States Patent
Ikeda

(10) Patent No.: US 7,407,742 B2
(45) Date of Patent: Aug. 5, 2008

(54) PLASMA OR SERUM SEPARATOR, PLASMA OR SERUM SAMPLING METHOD, PLASMA OR SERUM SEPARATING METHOD, TEST CARRIER AND GLASS FIBER

(75) Inventor: Eiji Ikeda, Tokyo (JP)

(73) Assignee: Sanko Junyaku Co., Ltd., Tokyo (JP)

( * ) Notice: Subject to any disclaimer, the term of this patent is extended or adjusted under 35 U.S.C. 154(b) by 482 days.

(21) Appl. No.: 10/505,557

(22) PCT Filed: Feb. 25, 2003

(86) PCT No.: PCT/JP03/02039

§ 371 (c)(1),
(2), (4) Date: Aug. 23, 2004

(87) PCT Pub. No.: WO03/073095

PCT Pub. Date: Sep. 4, 2003

(65) Prior Publication Data

US 2005/0106552 A1    May 19, 2005

(30) Foreign Application Priority Data

Feb. 27, 2002    (JP)    ............... 2002-051363

(51) Int. Cl.
*A01N 1/02*    (2006.01)
*C02F 1/44*    (2006.01)

(52) U.S. Cl. ............... 435/2; 210/348; 210/488; 210/490; 210/500.1; 210/503; 210/504; 210/505; 210/506; 210/507; 210/508; 210/767; 422/73; 422/101; 422/102; 422/104

(58) Field of Classification Search ............... 210/650, 210/651, 767, 321.6, 348, 488, 490, 500.1, 210/503, 504, 505, 506, 507, 508; 422/73, 422/101, 102, 104; 435/2

See application file for complete search history.

(56) References Cited

U.S. PATENT DOCUMENTS 2,837,170 A    6/1958    Francis ............... 55/524

(Continued)

FOREIGN PATENT DOCUMENTS

DE    1498577    4/1969

(Continued)

OTHER PUBLICATIONS

International Search Report for PCT/JP03/02039 mailed on Apr. 30, 2003.

*Primary Examiner*—John Kim
(74) *Attorney, Agent, or Firm*—Rader, Fishman & Grauer PLLC

(57) ABSTRACT

Provided are a plasma or serum separator and a plasma or serum sampling method capable of isolating plasma or serum with good efficiency from a small amount of blood without using a centrifuge and without causing leakage of a blood cell component or hemolysis, and in addition, capable of isolating and collecting plasma or serum from a whole blood test sample in a short time with simplicity in a blood test in the scene of medical care requiring an instant treatment any time such as an emergency test, home-use test or the like. The plasma or serum separator for isolating plasma or serum from whole blood comprises: a blood separation member, a holding member covering and holding the blood separation member; a blood introducing portion formed in a portion of the holding member covering a proximal end portion of the blood separation member; and a plasma or serum sampling aperture formed in a portion of the holding member covering a distal end portion of the blood separation member, wherein the whole blood is introduced into the blood separation member through the blood introducing portion, the introduced whole blood is separated such that the plasma or serum is located in the distal end portion of the blood separation member, while blood cells are located in the proximal end portion of the blood separation member; thereby enabling the plasma or serum located in the distal end portion of the blood separation member to be sampled through the plasma or serum sampling aperture.

26 Claims, 14 Drawing Sheets

FIG.5

U.S. PATENT DOCUMENTS

| | | |
|---|---|---|
| 3,146,163 A | 8/1964 | Brewer |
| 3,590,106 A | 6/1971 | Smith ..................... 264/136 |
| 4,753,776 A | 6/1988 | Hillman et al. |
| 4,816,224 A | 3/1989 | Vogel et al. |
| 5,055,195 A | 10/1991 | Trasch et al. |
| 5,262,067 A | 11/1993 | Wilk et al. |
| 5,665,238 A | 9/1997 | Whitson et al. |
| 5,725,774 A | 3/1998 | Neyer ..................... 210/645 |
| 5,979,669 A | 11/1999 | Kitajima et al. ............ 210/455 |
| 6,036,659 A | 3/2000 | Ray et al. ................. 600/573 |
| 6,220,453 B1 | 4/2001 | Kitajima et al. |
| 6,241,886 B1 | 6/2001 | Kitagawa et al. ........... 210/507 |
| 6,391,265 B1 | 5/2002 | Buechler et al. ........... 422/101 |

FOREIGN PATENT DOCUMENTS

| | | |
|---|---|---|
| EP | 0 305 803 A2 | 3/1989 |
| EP | 0 597 577 A1 | 5/1994 |
| JP | 53-72691 S | 6/1978 |
| JP | 60-011166 A | 1/1985 |
| JP | 60-036961 A | 2/1985 |
| JP | 61-038608 A | 2/1986 |
| JP | 61-118661 A | 6/1986 |
| JP | 61-207966 A | 9/1986 |
| JP | 64-021362 A | 1/1989 |
| JP | 02-140147 A | 5/1990 |
| JP | 04-208856 A | 7/1992 |
| JP | 05-196620 A | 8/1993 |
| JP | 07-005173 A1 | 1/1995 |
| JP | 10-185910 A1 | 7/1998 |
| JP | 10-211277 A1 | 8/1998 |
| JP | 11-038001 A1 | 2/1999 |
| JP | 11-295298 A1 | 10/1999 |
| JP | 2002-350428 A1 | 12/2002 |

FIG.3
(a)
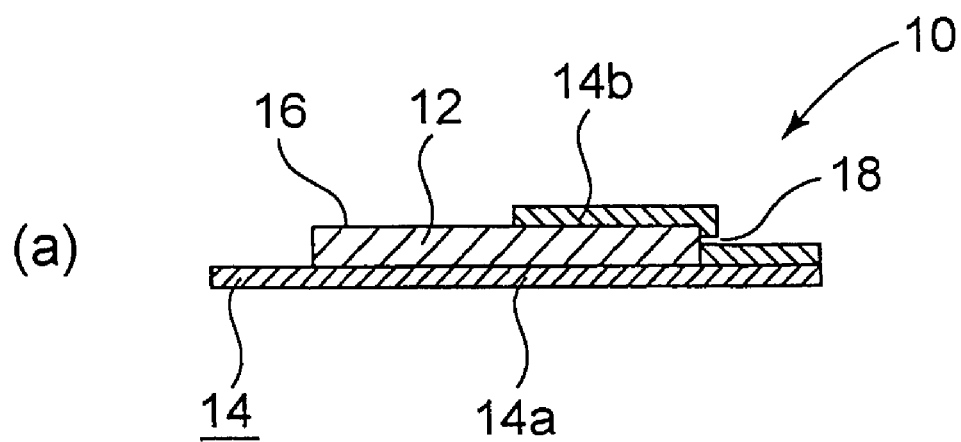
(b)
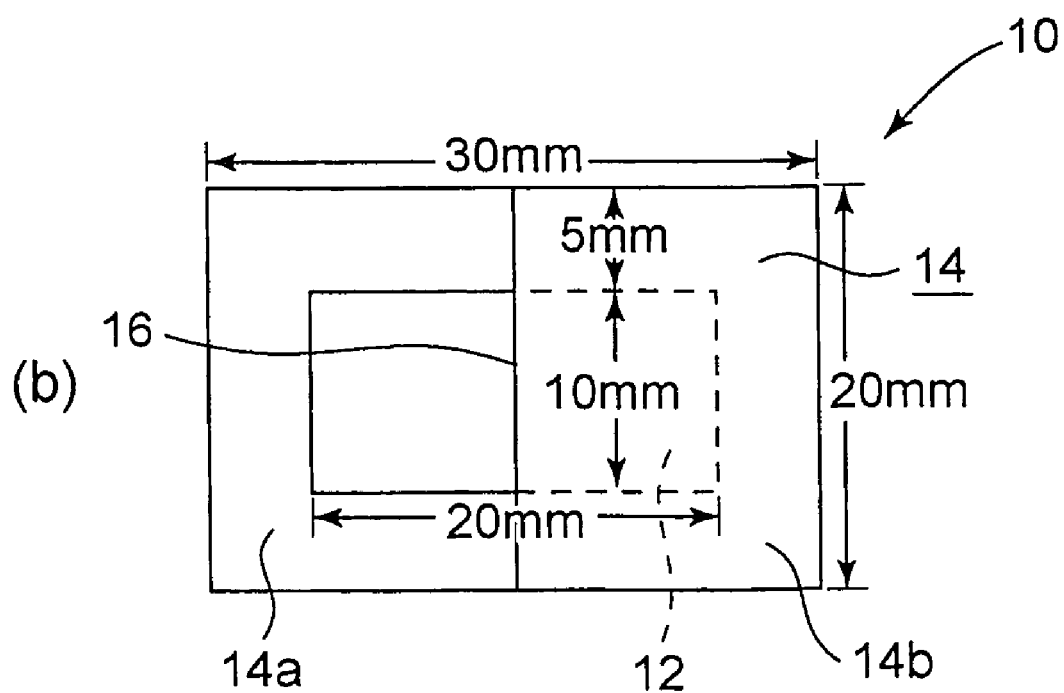

FIG.8
(a) 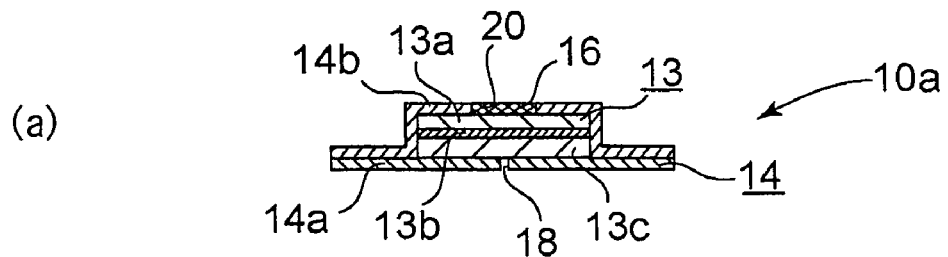
(b) 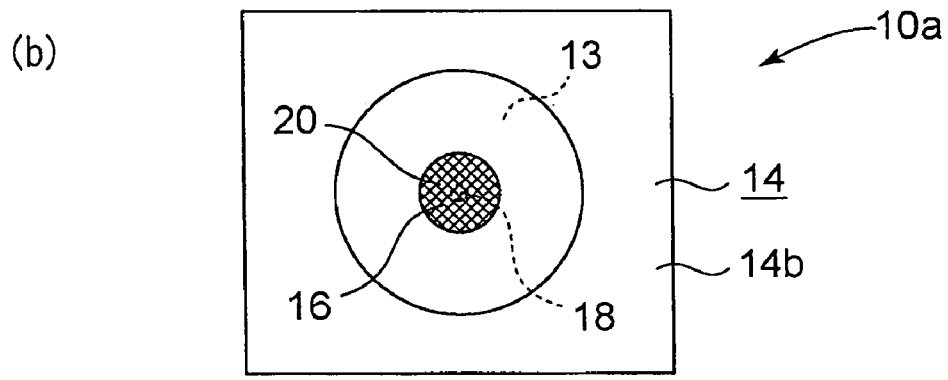
(c) 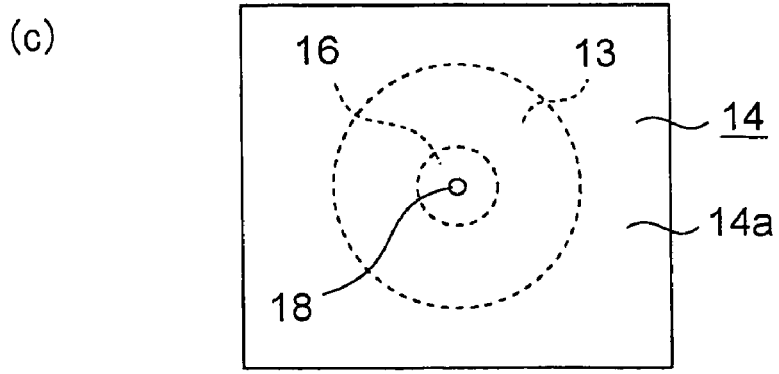

PLASMA OR SERUM SEPARATOR, PLASMA OR SERUM SAMPLING METHOD, PLASMA OR SERUM SEPARATING METHOD, TEST CARRIER AND GLASS FIBER

TECHNICAL FIELD

The present invention relates to a plasma or serum separator for isolating plasma or serum from whole blood and to a plasma or serum sampling method using the separator; particularly, to a plasma or serum separator and a plasma or serum sampling method, in a blood test, for rapidly isolating and sampling high purity plasma or serum in a liquid state or in a dry state even from a small amount of blood without using a centrifuge, to a plasma or serum separating method, to a test carrier and to glass fibers; and more particularly, to a plasma or serum separator for isolating plasma or serum from whole blood in which hemolysis is suppressed without using a centrifuge, to a plasma or serum separating method using the separator, to a test carrier having the separator, and to glass fibers.

BACKGROUND ART

In a clinical chemistry test and a clinical immunologic test, many of rapid tests for qualitative and quantitative diagnosis have been developed in the field of a hospital-related examination using blood as a sample.

Though part of the clinical tests can be carried out on whole blood, it is necessary to use plasma or serum isolated from a blood sample in order to attain a correct result of the test. If not isolated, red blood cells or an impurity in a blood sample blocks reflected light, transmitted light and emission measured in the test, affecting the measurement adversely.

Measurement on the kind and concentration of a blood component in a clinical laboratory test is usually performed such that whole blood is sampled with a blood collecting device, the sampled whole blood in a blood sampling tube is centrifuged to obtain serum or plasma and the obtained serum or plasma is used as a test sample.

Centrifugation, however, requires hundreds of µL or more of the whole blood amount and further consumes labor and time. Especially, in many fields of biochemical examinations, the presence of blood cells such as red blood cells disturbs the examinations; therefore, the serum or plasma is isolated from the blood in advance and used as a test sample. Hence, a necessity arises for a process in which blood sampled from a patient or a subject is at first coagulated in advance of an examination and then centrifuged to thereby obtain serum. While in Clinical Chemistry Analyzers available in recent years, a necessary mount of a test sample used in any of most examinations is as small as in the range of from several µL to tens of µL because of advancement in technology, a sampled blood amount depends on specifications of a centrifuge and a size of a blood sampling tube, which wastefully requires a blood amount more than necessary.

In the conventional centrifugal separation method, with a smaller test sample amount, separated red blood cells are re-suspended in plasma or serum; a problem arises that it is difficult to obtain only plasma or serum. therefore, in the centrifugal separation method, a test sample amount has to be in the range of from hundreds of µL to several mL, which necessitates a syringe to sample blood, having led to a fault that a great burden is imposed on a person to be examined. Furthermore, since the centrifugal separation method requires a special apparatus for centrifuging and is carried out only in batches, it is disadvantageous in cost for treatments on small number of test samples and unsuitable for an on-demand and instant treatment.

A method of measuring a bilirubin concentration of a neonate is such that a blood-sampling needle is stuck in a sole of the neonate to sample blood with a capillary tube. Sampled blood is separated to obtain serum or plasma by a centrifuge for capillaries and a bilirubin concentration is attained by conversion of an absorbance in the proximity of a wavelength in the range of from 450 to 460 nm, which is a bilirubin absorption wave length, measured with a photometer dedicated thereto as shown in FIG. 17. Therefore, in order to perform the examination, a centrifuge for exclusive use has been required and a time has been consumed in separating operation longer than in measurement itself.

In FIG. 17, reference numeral 50 designates a light source; 52, a optical light chopper; 54, a heat absorbing filter; 56, a lens; 58, a filter disk; 60a and 60b, interference filters; 62, a capillary tube; 64, a capillary tube holder; 66, a photodiode; 68, an amplifier; and 70, a meter. The capillary tube 62 in which plasma or serum isolated from blood is accommodated is to be held on the capillary tube holder 64 and light from the light source 50 is to be passed through the optical light chopper 52, the heat absorbing filter 54, the lens 56 and the interference filters 60a and 60b and is irradiated to the capillary tube 62, thereby an absorbance being measured at a wavelength in the proximity of a value in the range of from 450 to 460 nm with the photodiode 66 to detect a bilirubin concentration with the meter 70.

As a means to solve the above problem, there has been known dry chemistry. This test is conducted such that a small amount of blood is dropped onto a plate constructed with a plasma or serum separation layer, which is a fiber filter such as a filter made of glass fibers; and a reaction layer located in the lower layer, and then plasma or serum is isolated in the plasma or serum separation layer and a reaction and a color development occur in the lower layer, which is subjected to colorimetry. The dry chemistry is a simple and convenient method not requiring troublesome sampling of plasma or serum with a centrifuge, whereas the test can be applied only to a system foe exclusive use, in which the plasma or serum separation layer and the reaction layer is integrated into one piece. Since one plate can be used to measure only one examination item, plural plates are required for examining plural items; therefore, the dry chemistry is too expensive for its simplicity and convenience to be used widely.

Proposals have been made on methods each obtaining plasma or serum from blood without using a centrifuge (JP-A Nos. 53-72691, 60-11166 and the like). These methods have problems that separation is time consuming, red blood cells cause to clog and hemolysis occurs; they have not been put into practical use.

Various proposals have been made on a technique in which blood is flown through a layer made of a fiber filter under pressure to thereby isolate plasma or serum. Methods and tools disclosed in JP-A Nos. 61-38608, 4-208856 and 5-196620 can sample plasma or serum without using a centrifuge, whereas an amount of plasma or serum obtained is small. Consequently, the techniques have not been widely applied.

A method in which a conventional plasma or serum separating filter is employed has a problem that a special device or tool is required for pressurization or reducing a pressure for collecting plasma or serum and operations are troublesome.

As described above, there has not been available, in the current state, a tool exhibiting a sufficient performance in isolating a plasma or serum component from a small amount of blood to be used for a clinical laboratory test in a short time with good efficiency.

On the other hand, as described above, the following matters may be mentioned in the centrifugal separation method; it takes too much time for separation; it is difficult to sample serum or plasma after separation from a small amount of a whole blood sample; and a necessity arises for an auxiliary facility that is not generally usable outside of an examination room. For the reasons, the centrifugal separation method is perfectly improper for a test implemented by an expert except a clinical laboratory test engineer at a site, other than an examination room, in a point of care test, which is performed in a bed-side test, an emergency test and the like.

In order to avoid the problems, many techniques have been devised and proposed. In these techniques, generally many kinds of materials have been employed for fabricating a filter. As filter materials, there have been conventionally known film materials such as paper, textile, glass, synthetic fibers or the like, each of which has proper pore sizes.

For example, a method has been disclosed in U.S. Pat. No. 4,816,224, in which glass fiber filter paper and a porous film with a specific size are laminated. U.S. Pat. No. 4,753,776 is related to a device for separating plasma or serum from red blood cells by bringing whole blood into contact with a filter made of glass fibers capable of carrying a red blood cell aggregating agent, and teaches a method in which a thickness and diameter of the glass fiber filter is defined and there is fed to a capillary tube flow device plasma or serum isolated by capillary force from whole blood while the whole blood flows through the filter. In both methods, a practical isolated amount of plasma or serum is usually 25% or less, which causes clogging with ease.

Then, in U.S. Pat. No. 5,665,238, there has been disclosed a method in which serum is isolated with a layer made of a fiber filter such as a glass fiber filter having a pore size of 3 μm or less, and containing mannitol which is a polysaccharide at a content in the range of 1 to 40% and albumin at a content in the range of 0.1 to 15% to thereby achieve separation with a high yield, but this method has faults that no consideration is given to hemolysis and a time taken for separation is long.

In U.S. Pat. No. 3,146,163 and DE-A-1498577, another method is described in which whole blood is applied to a material coated with a red blood cell aggregating agent such as a vegetative red blood cell aggregating agent in order to isolate plasma or serum, and as carrier materials that can be used, there are named plastic and fibrous materials such as a card board.

In JP-A No. 61-118661, there has been disclosed a separation method for whole blood in which whole blood is treated with a matrix impregnated with lectin to isolate plasma or serum, wherein the matrix is an absorbing material having a relative resistance as high as 40% to a fluid flow. Furthermore, there are shown matrices each having a fibrous structure or a fiber structure, and having a resistance as small as possible to a fluid flow, and as preferable materials, there are exemplified cotton, viscose fibers and a cellulose material. An apparent fault of this method, however, is a necessity for washing separated plasma or serum from the matrix with a diluent.

In JP-A No. 64-21362, there has been disclosed still another apparatus isolating plasma or serum from whole blood. The apparatus contains an absorbing matrix having treated with a reagent aggregating blood cells, and thrombin or lectin is named as the reagent aggregating blood cells. As absorbing matrices, there are recommended hydrophobic powder, sponge, clay, fibers and a polymer, and fiber-containing paper is recognized as a polymer and a filter paper is a preferable matrix.

JP-A No. 61-207966 teaches a reagent for isolating plasma or serum from whole blood in a case where an absorbing matrix impregnated with lectin is used as a separation layer.

JP-A No. 2-140147 discloses that polycation is fixed on an absorbing solid material so as to create a cationic surface to which red blood cells are coupled when being brought into contact with whole blood, and paper is named as a preferable carrier material.

JP-A No. 60-36961 discloses that plasma or serum is isolated from whole blood using an absorbing porous material impregnated with a material having some polar groups. Examples of absorbing porous materials generally include paper, pad and fibers.

EP-A-0305803 discloses an apparatus for isolating red blood cells from a red blood cell containing body fluid, which comprises a fiber-containing filtration layer including a red blood cell aggregating antibody and if desired, lectin or a glass fiber filtration layer and lectin.

Of the known whole blood separating methods described above, especially practically effective is a method in which whole blood is brought into contact with a fiber containing layer having a red blood aggregating function to cause the fiber containing layer to hold red blood cells. A problem encountered in a case where a fiber-containing layer of this kind is employed is that hemolysis occurs if red blood cells are brought into contact with a fiber-containing layer.

On the other hand, a method disclosed in U.S. Pat. No. 5,262,067 is a good method in which a glass fiber layer containing a red blood cell aggregating material is coated with polyvinyl alcohol or polyvinyl alcohol/polyvinyl acetate to thereby enable hemolysis to be suppressed so as to give no practical influence on a plasma or serum component isolated from whole blood, but this method has a problem to take a long time for separation.

Hemolysis releases hemoglobin from a red blood cell to thereby decolorize plasma or serum. Since such decolorization can considerably disturb a colorimetric analysis, as hemolysis of red blood cells caused by glass is smaller in amount, a less influence of an inhibitor is exerted on measurement.

The present invention has been made in light of the above problems and it is an object of the present invention to provide a plasma or serum separator and a plasma or serum sampling method capable of isolating plasma or serum with good efficiency from a small amount of blood without using a centrifuge and without causing leakage of a blood cell component or hemolysis, and in addition, capable of isolating and collecting plasma or serum from a whole blood test sample in a short time with simplicity in a blood test in the scene of medical care requiring an instant treatment any time such as an emergency test, home-use test or the like.

The present inventor has conducted a study on subjects to find a possibility separating a cellular component in non-diluted blood, especially red blood cells from plasma or serum, to prevent hemolysis during the separating, to find a possibility of high speed separation during the separating and to enable the separating in a point of care test in a clinical laboratory test with the result of findings that to the present inventor's surprise, by using a fiber containing a layer including glass fibers coated with hexylene glycol, butoxypropanol or butoxymethylacrylamide as a plasma or serum separation layer, hemolysis does not substantially occur and the fiber containing layer is suited for separating very well a cellular component of non-diluted whole blood from plasma or serum, which has led to the present invention.

It is a second object of the present invention to provide a plasma or serum separating method of isolating-plasma or serum from whole blood, a separator, a test carrier, and glass fibers, in which not only is separation of red blood cells performed in a short time, but a separation ability is also high, and in addition less of hemolysis occurs.

DISCLOSURE OF THE INVENTION

A first aspect of a plasma or serum separator of the present invention, in order to solve the problem, is a plasma or serum separator for isolating plasma or serum from whole blood, which comprises: a blood separation member, a holding member covering and holding the blood separation member; a blood introducing portion formed in a portion of the holding member covering a proximal end portion of the blood separation member; and a plasma or serum sampling aperture formed in a portion of the holding member covering a distal end portion of the blood separation member, wherein the whole blood is introduced into the blood separation member through the blood introducing portion, the introduced whole blood is separated such that the plasma or serum is located in the distal end portion of the blood separation member, while blood cells are located in the proximal end portion of the blood separation member; thereby enabling the plasma or serum located in the distal end portion of the blood separation member to be sampled through the plasma or serum sampling aperture.

A second aspect of the present invention is a plasma or serum separator for isolating plasma or serum from whole blood, which comprises: a blood separation laminate having a first layer made of a blood separation member, a second layer made of a hemolysis blocking member and a third layer made of a plasma or serum absorbing member; a holding member covering and holding the blood separation laminate; a blood introducing portion formed in a portion of the holding member covering the first layer side of the blood separation member; and a plasma or serum sampling aperture formed in a portion of the holding member covering the third layer side of the blood separation member, wherein the whole blood is introduced into the blood separation laminate through the blood introducing portion, the introduced whole blood is separated such that the blood cells are located in the first layer, while the plasma or serum is absorbed and isolated in the third layer; thereby enabling the plasma or serum absorbed in the third layer to be sampled through the plasma or serum sampling aperture.

A third aspect of the present invention is a plasma or serum separator for isolating plasma or serum from whole blood, which comprises: a blood separation laminate having a first layer made of a blood separation member, a second layer made of a hemolysis blocking member and a third layer made of a plasma or serum absorbing member; a holding member covering and holding the blood separation laminate; a blood introducing portion formed in a portion of the holding member covering the first layer side of the blood separation member; wherein the third layer can be moved apart and disassembled from the first and second layers, the whole blood is introduced into the blood separation laminate through the blood introducing portion, the introduced whole blood is separated such that blood cells are located in the first layer, while the plasma or serum is absorbed and isolated in the third layer and the plasma or serum can be sampled by disassembling the third layer containing the plasma or serum.

In the third aspect of a plasma or serum separator of the present invention, it is preferable that the third layer not only can be moved apart and disassembled from the first and second layers, but can also be exposed to the outside air, wherein after the plasma or serum is absorbed and separated into the third layer, the third layer having absorbed the plasma or serum is exposed to the outside air to desiccate the absorbed plasma or serum, and the third layer containing the desiccated plasma or serum is disassembled.

Any kind of blood separation members may be used as far as it is a known material having a function capable of capturing blood cells without causing hemolysis and a blood separation member made of a fibrous material and/or a porous material can be employed.

The fibrous material and/or the porous material is one kind or two or more kinds selected from the group consisting of glass fibers, non-woven fabrics, cellulose fibers, polyester, polypropylene, polyamide, polyethylene, polyurethane and polyvinyl formal.

Any member may be used as the holding member as far as it can cover surfaces of a blood separation member without leaving any clearance and has a liquid non-penetrability, and a transparent or semi-transparent liquid non-penetrable film may be preferably used.

It is preferable to cover the blood introducing portion with a network member capable of being penetrated by blood.

A first aspect of a plasma or serum sampling method of the present invention employs the first aspect of a plasma or serum separator of the present invention and comprises the steps of: sticking a needle-like tool in the blood sampling portion to cause the portion to bleed; bringing the blood introducing portion of the plasma or serum separator into contact with the bleeding site to introduce whole blood into the blood separation member; subjecting the introduced whole blood to separation by the blood separation member such that the plasma or serum is located in the distal end portion thereof, while blood cells are located in the distal end portion thereof; and sampling the plasma or serum staying in the distal end portion of the blood separation member through the plasma or serum sampling aperture.

A second aspect of a plasma or serum sampling method of the resent invention employs the second aspect of the plasma or serum of separator of the present invention and comprises the steps of: sticking a needle-like tool in the blood sampling portion to cause the portion to bleed; bringing the blood introducing portion of the plasma or serum separator into contact with the bleeding site to introduce whole blood into the blood separation laminate, subjecting the introduced whole blood to separation such that blood cells are located in the first layer, while plasma or serum is absorbed and isolated in the third layer; and sampling the plasma or serum absorbed in the third layer through the plasma or serum sampling aperture.

A third aspect of a plasma or serum sampling method of the present invention employs the third aspect of the plasma or serum of separator of the present invention and comprises the steps of: sticking a needle-like tool in the blood sampling portion to cause the portion to bleed; bringing the blood introducing portion of the plasma or serum separator into contact with the bleeding site to introduce whole blood into the blood separation laminate; subjecting the introduced whole blood to separation such that blood cells are located in the first layer, while plasma or serum is absorbed and isolated in the third layer; and disassembling the third layer containing the plasma or serum to thereby enable the plasma or serum to be sampled.

In the third aspect of a plasma or serum sampling method of the present invention, after the plasma or serum is absorbed and isolated in the third layer, the third layer having absorbed the plasma or serum is exposed to the outside air to desiccate the absorbed plasma or serum, and the third layer containing the desiccated plasma or serum is disassembled to thereby enable the plasma or serum to be sampled. Furthermore, after the third layer having absorbed the plasma or serum is disassembled, the plasma or serum can be similarly desiccated, which is the same aspect.

A fourth aspect of a plasma or serum separator of the present invention is a device isolating plasma or serum from whole blood which comprises: a fibrous material and/or a porous material coated with one kind or two or more kinds selected from the group consisting of hexylene glycol, propanol with a butoxy group and acrylamide with a butoxy group as a blood separation member.

The plasma or serum separator can suppress hemolysis by bringing whole blood into contact with the blood separation member to hold red blood cells in the blood separation member and to thereby isolate the plasma or serum in the whole blood.

A plasma or serum separating method of the present invention is a method of isolating plasma or serum from whole blood by bringing the whole blood into contact with a blood separation member to hold red blood cells in the blood separation member, wherein hemolysis is suppressed by using the fourth aspect of the plasma or serum separator of the present invention.

A test carrier of the present invention comprises: a plasma or serum separation layer for isolating plasma or serum from a blood sample component and a test region for testing the isolated plasma or serum, wherein the plasma or serum separation layer comprises the plasma or serum separator described above to thereby suppress hemolysis.

The fibrous material and/or the porous material may include one kind or two or more kinds selected from the group consisting of glass fibers, non-woven fabrics, cellulose fibers, polyester, polypropylene, polyamide, polyethylene, polyurethane and polyvinyl formal.

Especially preferable are glass fibers coated with one kind or two or more kinds selected from the group consisting of hexylene glycol, propanol with a butoxy group and acrylamide with a butoxy group.

Butoxypropanol is preferable as propanol with a butoxy group and butoxymethylacrylamide is preferable as acrylamide with a butoxy group.

Glass fibers of the present invention are coated with one kind or two or more kinds selected from the group consisting of hexylene glycol, propanol with a butoxy group and acrylamide with a butoxy group.

BRIEF DESCRIPTION OF THE DRAWINGS

FIG. 3 shows a third embodiment of a plasma or serum separator of the present invention, wherein the part (a) is a schematic sectional view thereof and the part (b) is a schematic top plan view thereof.

FIG. 8 shows a fourth embodiment of a plasma or serum separator of the present invention, wherein the part (a) is a schematic sectional view thereof, the part (b) is a schematic top plan view thereof and the part (c) is a schematic bottom view thereof.

BEST MODE FOR CARRYING OUT THE INVENTION

Description will be given of one embodiment of the present invention below based on the accompanying drawings and it is needless to say that the examples shown in the figures are shown by way of illustration only and various modification or variations can be implemented as far as not departing from the technical concept of the present invention.

Figure 1:
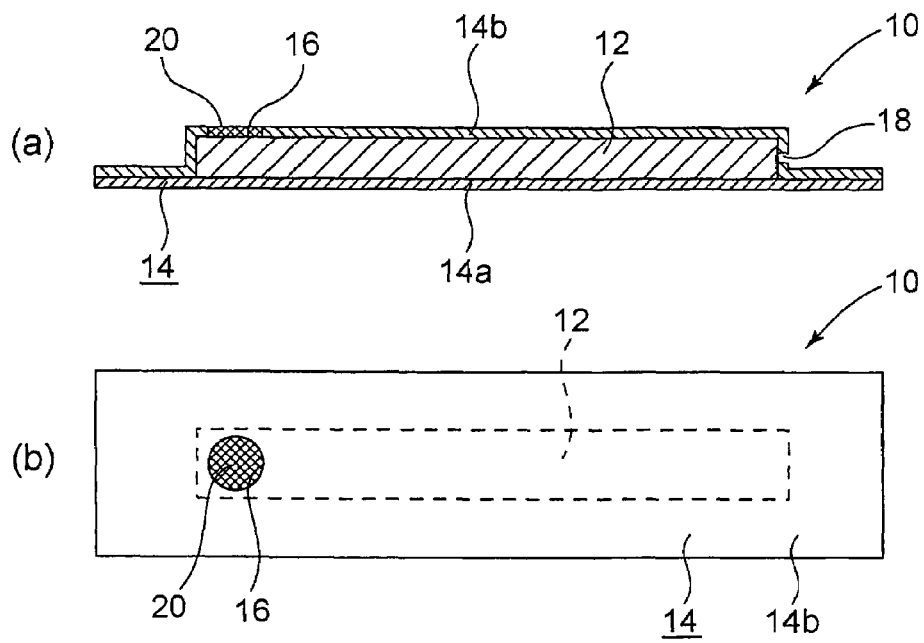
FIG. 1 shows a first embodiment of a plasma or serum separator of the present invention, wherein the part (a) is a schematic sectional view thereof and the part (b) is a schematic top plan view thereof.

FIG. 1 shows a first embodiment of a plasma or serum separator of the present invention, wherein the part (a) is a schematic sectional view thereof and the part (b) is a schematic top plan view thereof. In FIG. 1, reference numeral 10 designates a plasma or serum separator according to the present invention. The plasma or serum separator 10 has a blood separation member 12 and the blood separation member 12 is covered and held by a holding member 14. The holding member 14 includes a base film ember 14a in the lower side and a covering film 14 in the upper side, the blood separation member 12 being fixedly sandwiched between the base film 14a and covering film 14b. When fixedly covering and holding the blood separation member 12 with the holding member 14, by adhering them without leaving any clearance therebetween, it is possible to isolate high purity plasma or serum from whole blood. A blood introducing portion 16 is formed on the upper surface of a proximal end portion of the covering film 14b and a plasma or serum sampling aperture 18 is perforated in a distal end portion of the holding member 14 on the opposite side thereof of the blood introducing portion 16.

Reference numeral 20 designates a network member covering the blood introducing portion 16. Since the blood separation member 12 exposed to the outside at the blood introducing portion 16 is covered with provision of the network member 20, the blood separation member 12 is protected from damage or the like. Any material may be used as the network member 20 as far as it does not become spherical by the action of surface tension as a result of blood permeation, and a plastic material such as nylon can be used.

Figure 2:
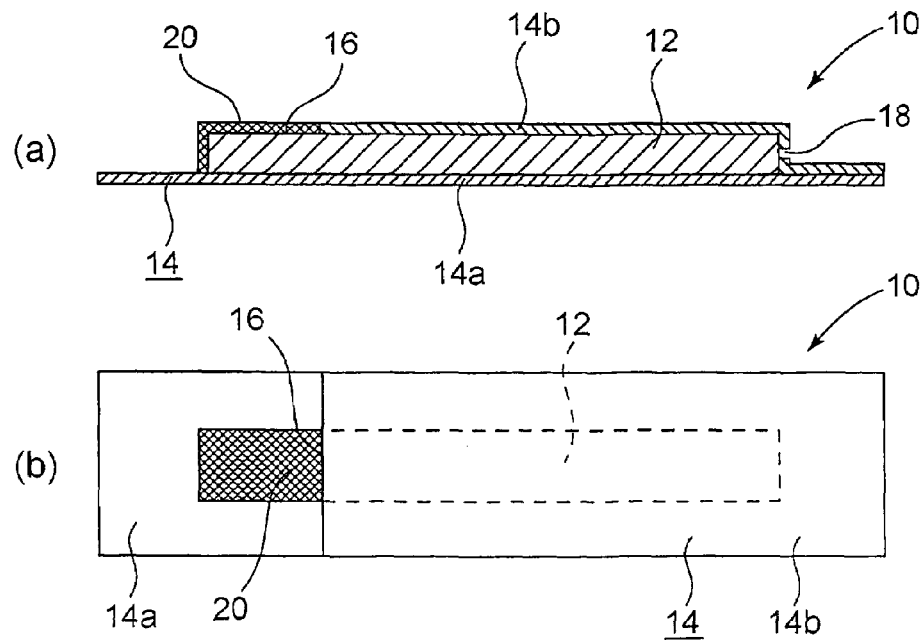
FIG. 2 shows a second embodiment of a plasma or serum separator of the present invention, wherein the part (a) is a schematic sectional view thereof and the part (b) is a schematic top plan view thereof.

The shape of the blood introducing portion 16 is not specifically limited and may be either a circle as shown in FIG. 1(b) or any of other shapes such as polygons. For example, as shown in FIG. 2 (the second embodiment) and FIG. 3 (the third embodiment), the shape of the blood introducing portion 16 can also be formed in such a way that the proximal end portion of the covering film 14b is all peeled off to form a large opening portion.

Although the blood introducing portion 16 is preferably covered with the network member 20, it is needless to say that the function and result of he present invention can be achieved even in a state where the blood separation member 12 is exposed to the outside air without providing the network member 20 as shown in FIG. 3.

The plasma or serum sampling aperture 18 may be perforated on the upper surface of the holding member 14, on the bottom surface thereof, or on any portion of side surfaces of the distal end portion without any specific limitation. A size of the plasma or serum sampling aperture 18 is preferably a circle of from 0.02 mm to 1 mm in diameter or a square equivalent thereto. A method of forming the plasma or serum sampling aperture 18 is not specifically limited and the aperture 18 is preferably formed by perforating the covering film 14b covering the blood separation member 12 using a needle-like tool such as a syringe needle.

The fibrous materials and/or porous materials used as the blood separation member 12 can include: inorganic fibers such as glass fibers and asbestos; natural organic fibers such as cotton, pulp, silk and the like; semi-synthetic fibers or synthetic fibers such as cellulose, cellulose acetate, polyester, polypropylene, polyurethane, polyamide, polyvinyl formal, polyethylene, polyvinyl chloride, viscose rayon and the like.

A glass fiber filter is preferably made of borosilicate glass with an average pore size in the range of from 3 to 6 µm and a preferable glass fiber membrane with the specification available on the market is of the GF/D type (manufactured by Whatman Inc.)

There may be included in the plasma or serum separation member either alone or jointly red blood aggregating materials, for example, known red blood cell aggregating materials such as cation polymer, lectin, an antibody for red blood cells and the like.

As the blood separation member, there is preferably used materials containing the fibrous materials and/or porous materials coated with coating materials such as hexylene glycol, propanol with a butoxy group and acrylamide with a butoxy group. The coating materials may be used either alone or jointly of two or more kinds. Especially, as a glass fiber filter, it is preferably used glass fibers coated with one kind or two or more kinds selected from the group consisting of hexylene glycol, propanol with a butoxy group and acrylamide with a butoxy group.

By using glass fibers coated with hexylene glycol; and/or a butoxypropanol, for example, 1-butoxy-2-propanol, which is a propanol with a butoxy group as a functional group; and/or a butoxymethylacrylamide, for example, N-butoxymethyl acrylamide, which is an acrylamide with a butoxy group, hemolysis in a separation process can be restricted to a practically non-problematical amount and separation of plasma or serum from red blood cells starts simultaneously with dropping of blood, thereby quick separation being realized.

A coating amount of hexylene glycol; and/or a propanol with a butoxy group; and/or an acrylamide with a butoxy group relative to glass fibers is 0.05 wt %, preferably 0.1 wt % and more preferably 0.2 wt % as the lower limit and 3.0 wt %, preferably 2.0 wt % and more preferably 1.5 wt % as the upper limit.

As a method of coating glass fibers with a red blood cell aggregating material, a method is preferable in which a blood separation member made of glass fiber filter is impregnated with a coating material in solution and the impregnation is, for example, conducted by applying an impregnating solution to a glass fiber filter or immersing it in the solution.

An amount of an impregnating solution is preferably in the range of from 0.3 wt % to 2.0 wt % and if the amount exceeds the range, a capillary force between the glass fibers is affected to release hemoglobin from red blood cells in hemolysis and extend a delay time for development of blood.

A preferable method in which the glass fiber filter is coated with hexylene glycol; and/or a propanol with a butoxy group; and/or an acrylamide with a butoxy group is such that a glass fiber filter paper is immersed in an impregnating solution including hexylene glycol, N-butoxymethyl acrylamide or 1-butoxy-2-propanol and then taken out, followed by desiccating it at a temperature in the range of from room temperature to 90° C. A desiccating time is in the range of from 25 to 80 min at a temperature in the range of from 50° C. to 90° C., which is practically non-problematical.

A size of the blood separation member 12 is required to be at least of a volume corresponding to a blood sample amount. A shape thereof is not specifically limited and may be any selected from the group consisting of a quadrangle, a triangle, other polygons, a circle, an ellipse, a shape of a tapered battledore plate with a narrower distal end and the like. While there is preferably used the shape of a box as shown in FIGS. 1 and 2, a blood separation member 12 whose distal end portion is narrower in shape is preferable because of easiness with which red blood cells are separated from plasma or serum. As to a thickness of the blood separation member there is a necessity that in order to separate a blood cell portion from a plasma or serum portion in whole blood, the blood cell portion is caused to remain in the blood separation member in whole blood supplied from the blood introducing portion, and the plasma or serum portion is caused to migrate in a traverse direction, that is in a direction toward the plasma or serum sampling aperture, and hence the thickness of the blood separation member 12 is set such that the blood separation member is filled with the blood cell portion from the upper surface to the bottom surface thereof and plasma or serum flows in the traverse direction in the blood cell separation member. A size of the blood separation member has only to be properly determined based on an amount of plasma or serum necessary for an examination without a specific limitation thereon.

In a case where a blood sampling needle is stuck in a hand, a foot or the like to sample blood, a blood amount that can be sampled is in the range of from about 25 to about 100 μL and a thickness and other dimensions are properly determined according to a blood amount to be sampled. For example, in a case of a blood amount of 25 μL, the thickness is preferably in the range of from 0.1 to 0.6 mm and in a case of a blood amount of 100 μL, the thickness is preferably in the range of from 0.1 to 1.4 mm.

The holding member 14 may be any of members capable of covering the surfaces of the blood separation member 12 without leaving any clearance and having a liquid non-penetrating property. The covering film 14b in at least a region at the distal end of the holding member 14 where plasma or serum is isolated has to be soft so as to enable blood to be pushed out. It is preferable to use a transparent or semi-transparent, liquid non-penetrating film as the holding member 14 because migration of blood and isolation of plasma or serum can be confirmed. The base film 14a and covering film 14b may be either the same material as or different from each other. As the holding member 14, preferably used is, for example, a pressure sensitive adhesive tape obtained by coating a pressure sensitive adhesive on a plastic film. The following plastic films can be used either alone or jointly: polyester film such as polyethylene terephthalate, polypropylene, polyethylene, polyvinyl chloride and the like. A thickness of the holding member 14 is not specifically limited and preferably on the order of 100 μm.

A plasma or serum separating method of the present invention employs the plasma or serum separator and thereby, plasma or serum can be efficiently isolated from even a small amount of blood without leaking a blood cell component or causing hemolysis.

Figure 4:
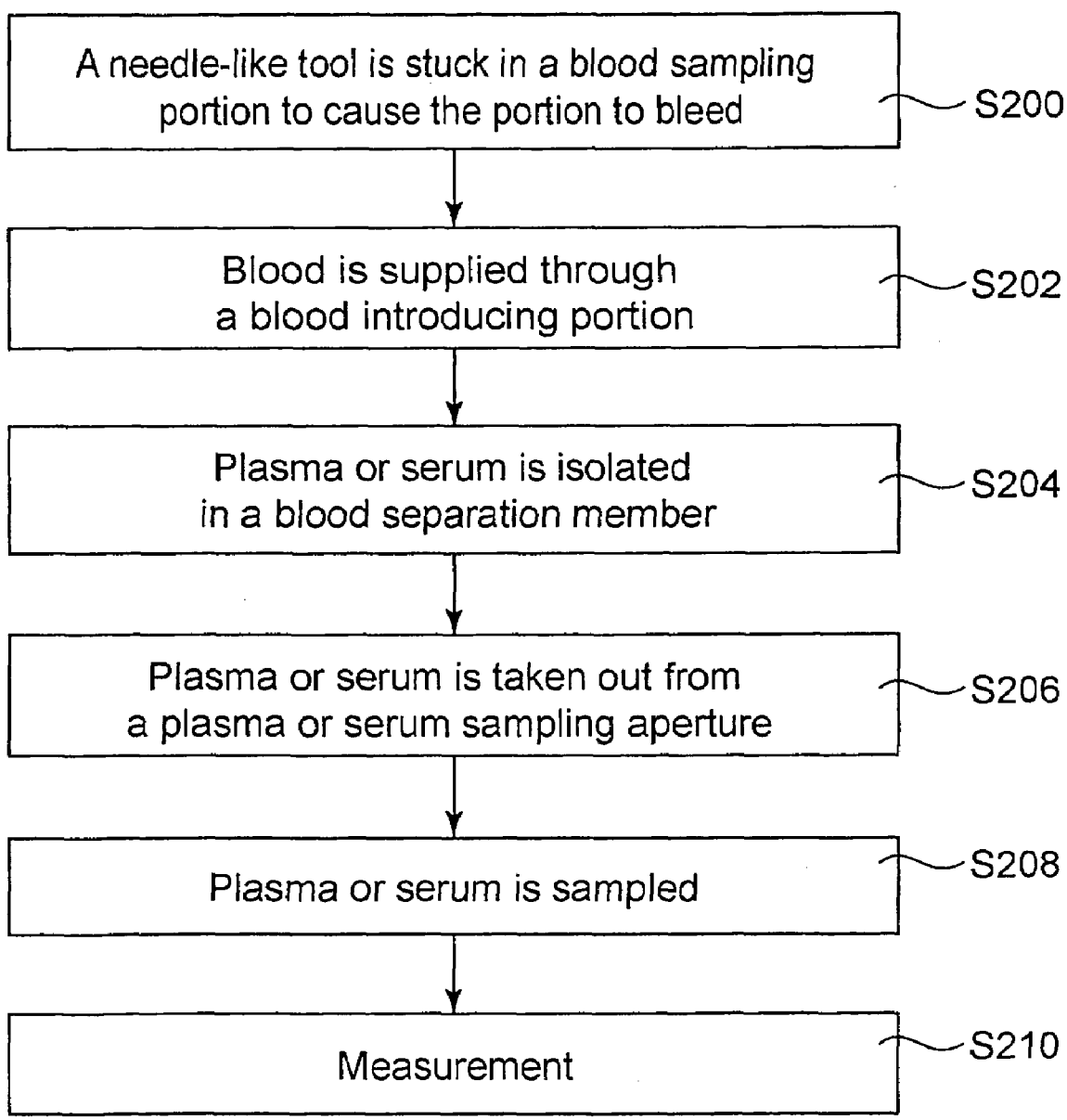
FIG. 4 is a flowchart showing one example of a process sequence according to a first aspect of a plasma or serum sampling method of the present invention.

FIG. 4 is a flowchart showing one example of a process sequence of the first aspect of a plasma or serum sampling method of the present invention using the first aspect (corresponding to the first to third embodiments) of a plasma or serum separator of the present invention described above, and FIG. 5 is a descriptive view showing each step of FIG. 4.

Figure 5:
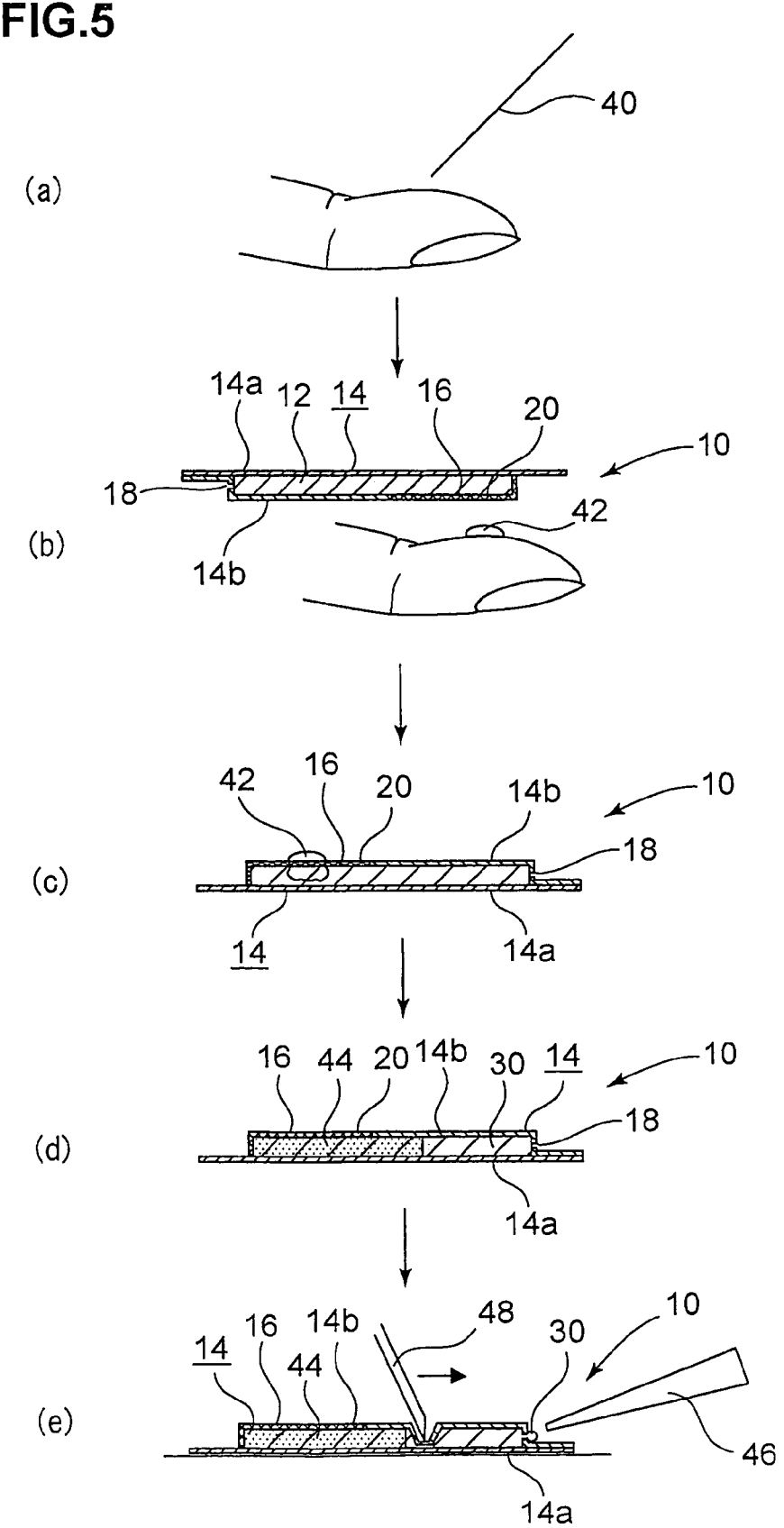
FIG. 5, consisting of FIGS. 5(a) to 5(e), is a descriptive schematic view showing one example of a process sequence according to a first aspect of a plasma or serum sampling method of the present invention.

In the first aspect of a plasma or serum sampling method according to the present invention, as shown in FIG. 4 and FIG. 5, a lancing device, for example a lancet 40, is at first stuck in a blood sampling portion to cause the portion to bleed (step 200 in FIG. 4 and FIG. 5(a)). The blood sampling portion is not specifically limited and for example, a hand, a foot or the like is preferably selected. After the bleeding, the blood introducing portion 16 or the network member 20 of the plasma or serum separator 10 of the present invention is brought into contact with the bleeding site to sample blood 42 and to supply the blood 42 through the blood introducing portion 16 (step 202 n FIG. 4 and FIG. 5(b), (c)).

In this case, the blood separation member 12 covered with the holding member 14 does not absorb any more of the blood after the blood separation member 12 is filled with plasma or serum isolated from red blood cells even if the blood 42 is further supplied.

The absorbed blood 42 migrates in the blood separation member 12 from the blood introducing portion 16 to the plasma or serum sampling aperture 18 at the distal end portion and a difference in migrating speed between plasma or serum and red blood cells is used so that red blood cells 44 is isolated in the blood introducing portion 16 side while plasma or serum 30 is isolated in the plasma or serum sampling aperture 18 side; thereby plasma or serum being isolated in the blood separation member 12 (step 204 in FIG. 4 and FIG. 5(d)).

With the holding member 14, especially the covering film 14b being transparent or semi-transparent, the separation process can be visually confirmed through the covering film 14b. A sampling amount of plasma or serum is determined by a hematocrit value of the blood and a plasma or serum separation ability of the blood separation member 12, and for example, in a case of a blood amount of 25 μL, plasma or serum in the range of from 5 to 12 μL flows from the blood introducing portion 16 in the traverse direction, that is in a direction toward the plasma or serum sampling aperture 18, in a time in the range of from 40 to 180 sec, during which separation is effected.

The isolated plasma or serum 30 can be taken out in the form of a liquid sphere from the plasma or serum sampling aperture 18 in the distal end portion (step 206 in FIG. 4 and FIG. 5(e)). The taken-out plasma or serum is sampled using a quantitative pipet 46, a capillary tube or the like (step 208) and necessary examination is performed on the sample (step 210 in FIG. 4).

How to take out the plasma or serum is not specifically limited. As shown in FIG. 5(e), by pressing the holding member 14 in the plasma or serum side of the boundary between the blood 44 and the plasma or serum 30 in the direction of the plasma or serum sampling aperture 18 side from the blood introducing portion 16 side using a tool 48, a finger or the like, plasma or serum can be easily discharged. To be more concrete, for example, it is only required that in the state that the bottom surface of the holding member 14 is firmly kept, for example, located on a flat surface and the upper surface thereof is pressed with a fingernail or a hard tool 48, by moving the fingernail or the hard tool 48 in the direction of the distal end portion shown by an arrow, the plasma or serum 30 is squeezed out to the plasma or serum sampling aperture 18 and sampled with a quantitative pipet 46, a capillary tube or the like.

Various kinds of sampling methods of plasma or serum 30 are conceived in addition to the methods described above and, for example, as shown in FIG. 6, a method can be adopted in which in the state that the upper surface and bottom surface are pressed with fingers without using a pressing device, by moving a fingernail in the direction shown by an arrow, the plasma or serum 30 is squeezed out to the plasma or serum sampling aperture 18 and sampled with a quantitative pipet, a capillary tube 32 or the like. Furthermore, as shown in FIG. 7, another method can be adopted in which in. the state that the holding member is pressed with a roller type device, by moving the roller 34 in the direction shown by an arrow, the plasma or serum 30 is squeezed out to the plasma or serum sampling aperture 18 and sampled with a quantitative pipet, a capillary tube 32 or the like.

In still another example of a method of squeezing plasma or serum, it is also possible that the plasma or serum is suctioned and sampled using a suction tool such as a pipet through the blood or serum sampling aperture 18.

Figure 17:
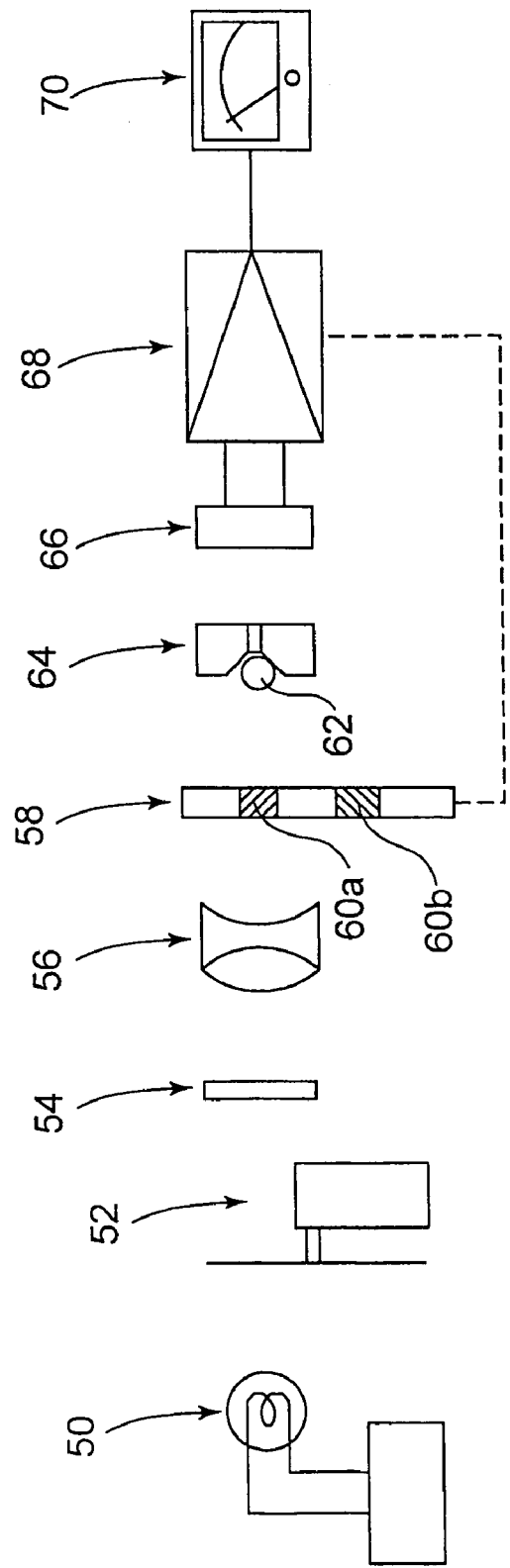
FIG. 17 is schematic descriptive view showing one example of a bilirubin analyzer for exclusive capillary tube use.

Plasma or serum sampled by the above methods can be used for any blood test without any specific limitation. For example, in a case where the plasma or serum sample is used for a measuring examination of a bilirubin concentration, it is preferable to sample the plasma or serum with a capillary tube and to measure it by a bilirubin analyzer for exclusive capillary tube use (FIG. 17). Plasma or serum sampled using a plasma or serum separator of the present invention does not differ from plasma or serum sampled using a common centrifuge, and then can be used for every blood test using plasma or serum including a biochemical examination.

With a plasma or serum separator and a plasma or serum sampling method of the present invention, high purity plasma or serum can be easily obtained from a small amount of blood without the use of a centrifuge. With a plasma or serum separator and a plasma or serum sampling method of the present invention, plasma or serum of a liquid state which is not desiccated can be obtained; therefore, the plasma or serum can be directly subjected to a quantitative analysis.

In each of the first to third embodiments of a plasma or serum separator of the present invention, there is shown a case where using the plasma or serum separation member 12 in the form of a flat plate, the plasma or serum and the blood cells are separated each other in the distal end portion and the proximal end portion, respectively, that is in a horizontal direction, but a separation direction is not limited to the horizontal direction, and can be in a vertical direction (downward and upward), which will be described below.

FIG. 8 shows a fourth embodiment (the second aspect) of a plasma or serum separator of the present invention, the part (a) is a schematic sectional view, the part (b) is a schematic top plan view and the part (c) is a schematic bottom view. In FIG. 8, the same or similar parts or members as those in FIGS. 1 to 3 are designated by the same reference numerals used in FIGS. 1 to 3.

In FIG. 8, reference numeral 10a designates a plasma or serum separator according to the present invention. The plasma or serum separator 10a has a blood separation laminate 13 and the blood separation laminate 13 is covered and held by a holding member 14. The holding member 14 includes a base film 14a in the lower side and a covering film 14b in the upper side and the blood separation laminate 13 is fixedly sandwiched between the base film 14a and the covering film 14b. When the blood separation laminate 13 is fixedly covered and held by the holding member 14, it is preferable to adhere them to each other without leaving any clearance, which is similar to that in the case of FIG. 1. Material of the holding member 14 is similar to that in the case of FIG. 1 and in the fourth embodiment of a plasma or serum separator 10a of the present invention, it is required to bend the plasma or serum separator 10a when plasma or serum is taken out as shown in FIG. 10(e); therefore it is necessary to use a bendable material for the holding member 14.

The blood separation laminate 13 is composed of a first layer 13a made of a blood separation member, a second layer 13b made of a hemolysis blocking member and a third layer 13c made of a plasma or serum absorbing member. The first layer 13a exerts blood separation action and is made of material similar to that of the blood separation member 12 shown in FIG. 1. The second layer 13b exerts blocking action so that hemolysis does not spread to the third layer 13c and is made of porous film materials such as nitrocellulose and Cyclopore (manufactured by Whatman Inc.). Pore sizes of the porous film can be of the order in the range of from 0.02 μm to 1.2 μm and preferably in the range of from 0.2 μm to 0.45 μm. The third layer 13c exerts absorbing action of the isolated plasma or serum and is made of water-absorbing materials such as glass fibers, cellulose, non-woven fabrics, filter paper or the like.

A blood introducing portion 16 is formed in a covering film 14b covering the first layer 13a side of the blood separation laminate 13. A plasma or serum sampling aperture 18 is open in a base film 14a covering the third layer 13c side of the blood separation laminate 13. Reference numeral 20 designates a network member covering the blood introducing portion 16. As stated before, no specific limitation is placed on a shape of the blood introducing portion 16. A size of the plasma or serum sampling aperture 18 is preferably of a circle in the range of from 0.02 mm to 1 mm in diameter or of a square equivalent in size to the circle.

Figure 9:
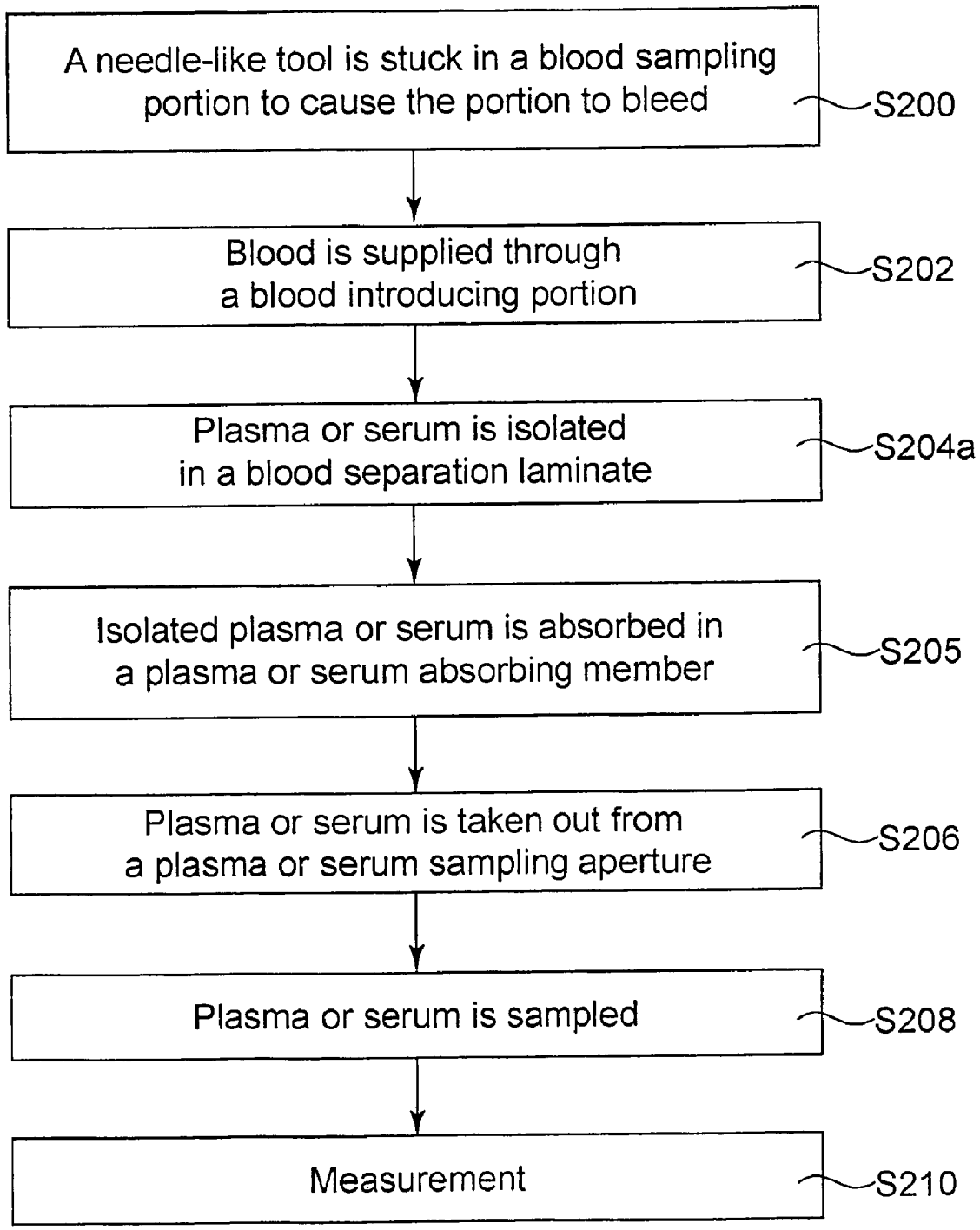
FIG. 9 is a flowchart showing one example of a process sequence according to a second aspect of a plasma or serum sampling method of the present invention.
Figure 10:
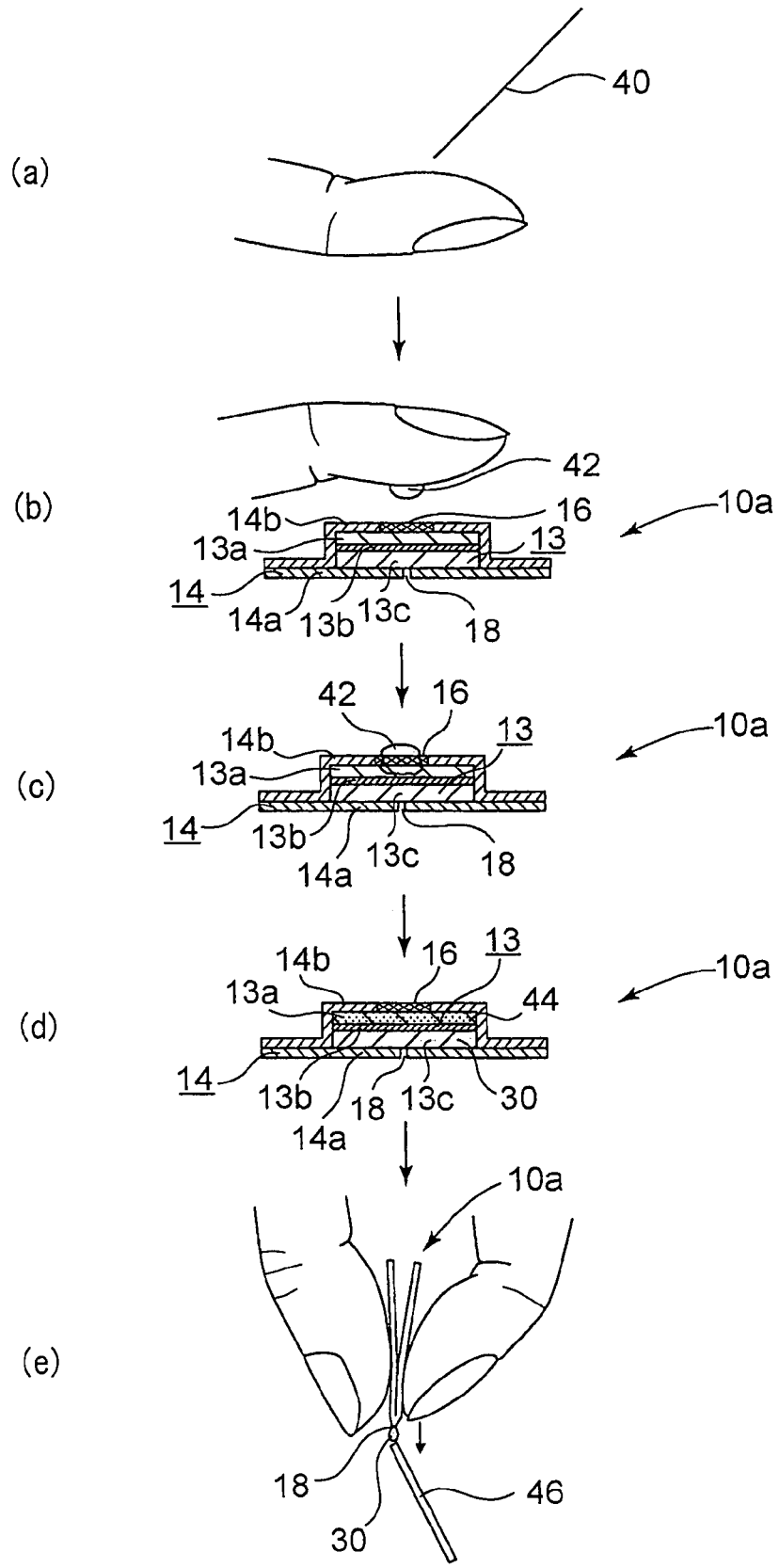
FIG. 10, consisting of FIGS. 10(a) to 10(e), is a descriptive schematic view showing one example of a process sequence according to a second aspect of a plasma or serum sampling method of the present invention.

FIG. 9 is a flowchart showing one example of the second aspect of a plasma or serum sampling method of the present invention using the fourth embodiment of a plasma or serum separator of the present invention and FIG. 10 is a descriptive schematic view showing each step in FIG. 9.

As shown in FIGS. 9 and 10, the second aspect of a plasma or serum sampling method according to the present invention is similar to a process up to the steps shown in FIGS. 4 and 5 where the needle-like tool is stuck in the blood sampling portion to cause the portion to bleed (step 200 in FIG. 9 and FIG. 10(a)) and then blood is supplied from the blood introducing portion (step 202 in FIG. 9 and FIGS. 10(b) and 10(c)).

Plasma or serum 30 in blood 42 introduced into the first layer (blood separation member) 13a of the blood separation laminate 13 migrates to and absorbed into the third layer (plasma or serum absorbing member) 13c by an absorbing action of the third layer 13c. On the other hand, blood cells 44 remain in the first layer (blood separation member) 13a. The blood cells 44 and the plasma or serum 30 are separated into the first layer 13a and the third layer 13c, respectively, through the second layer 50b (steps 204a and 205 in FIG. 9 and FIG. 10(d)). The plasma or serum 30 isolated and absorbed in the third layer 13c can be taken out in the form of a liquid sphere from the plasma or serum sampling aperture 18 by bending the plasma or serum separator 10a, as shown in FIG. 10(e), so that the plasma or serum sampling aperture 18 becomes an outward bending point (step 206 in FIG. 9). The taken out plasma or serum is sampled with a quantitative pipet, a capillary tube or the like (step 208 in FIG. 9), then a necessary examination being carried out (step 210 in FIG. 9).

Figure 11:
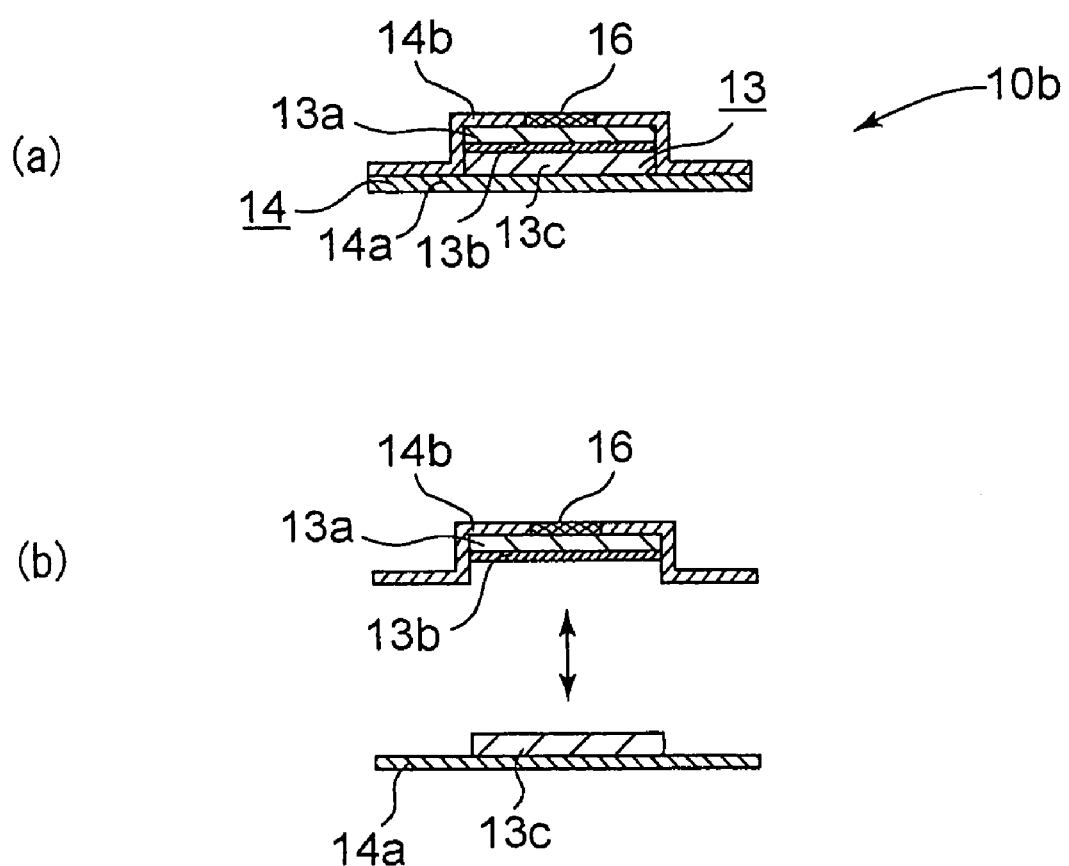
FIG. 11 shows a fifth embodiment of a plasma or serum separator of the present invention, wherein the part (a) is a schematic sectional view thereof and the part (b) is a schematic sectional view in a state where a plasma or serum absorbing material is disassembled.

In the fourth embodiment of a plasma or serum separator of the present invention, a feature resides in that isolation of plasma or serum is carried out using the plasma or serum separation laminate 13. Using the plasma or serum laminate 13, the plasma or serum 30 is absorbed, isolated and held in the third layer (plasma or serum absorbing member) 13c. Therefore, if the third layer 13c can be separated and disassembled from the first and second layers 13a and 13b of the plasma or serum separation laminate 13 as the plasma or serum separator 10b shown in FIG. 11, the plasma or serum 30 can be simply desiccated by disassembling the third layer 13c in a state where the plasma or serum 30 is absorbed and held from the plasma or serum separation laminate 13 to expose the third layer 13c to the outside air. Thus, by disassembling only the third layer 13c holding the plasma or serum in a desiccated state, there becomes available various kinds of ways to handle the plasma or serum 30 in a desiccated state. For example, the plasma or serum in a desiccated state has such an advantage to be capable of being kept for a long time and of being transported by mail or the like means to a remote site of examination. In the plasma or serum separator 10b shown in FIG. 11, since the plasma or serum 30 absorbed in the third layer 13c is not pressed out for sampling it as a solution, it is not necessary to provide a plasma or serum sampling aperture 18. Since the plasma or serum 30 absorbed in the third layer 13c is desiccated, a structure can also be adopted in which a hole having a large diameter exposed to the outside air is formed in the base film 14a in advance.

Figure 12:
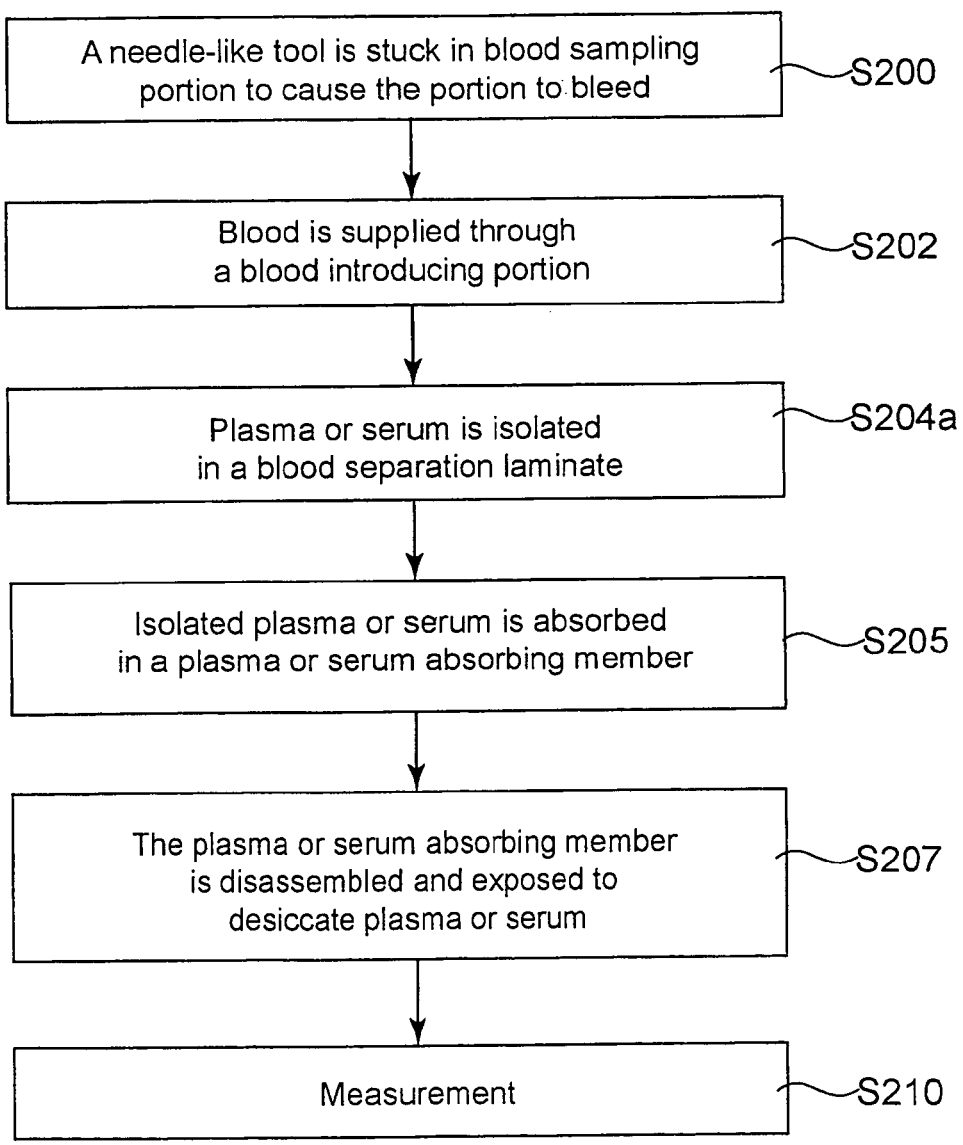
FIG. 12 is a flowchart showing one example of a process sequence according to a third aspect of a plasma or serum sampling method of the present invention.
Figure 13:
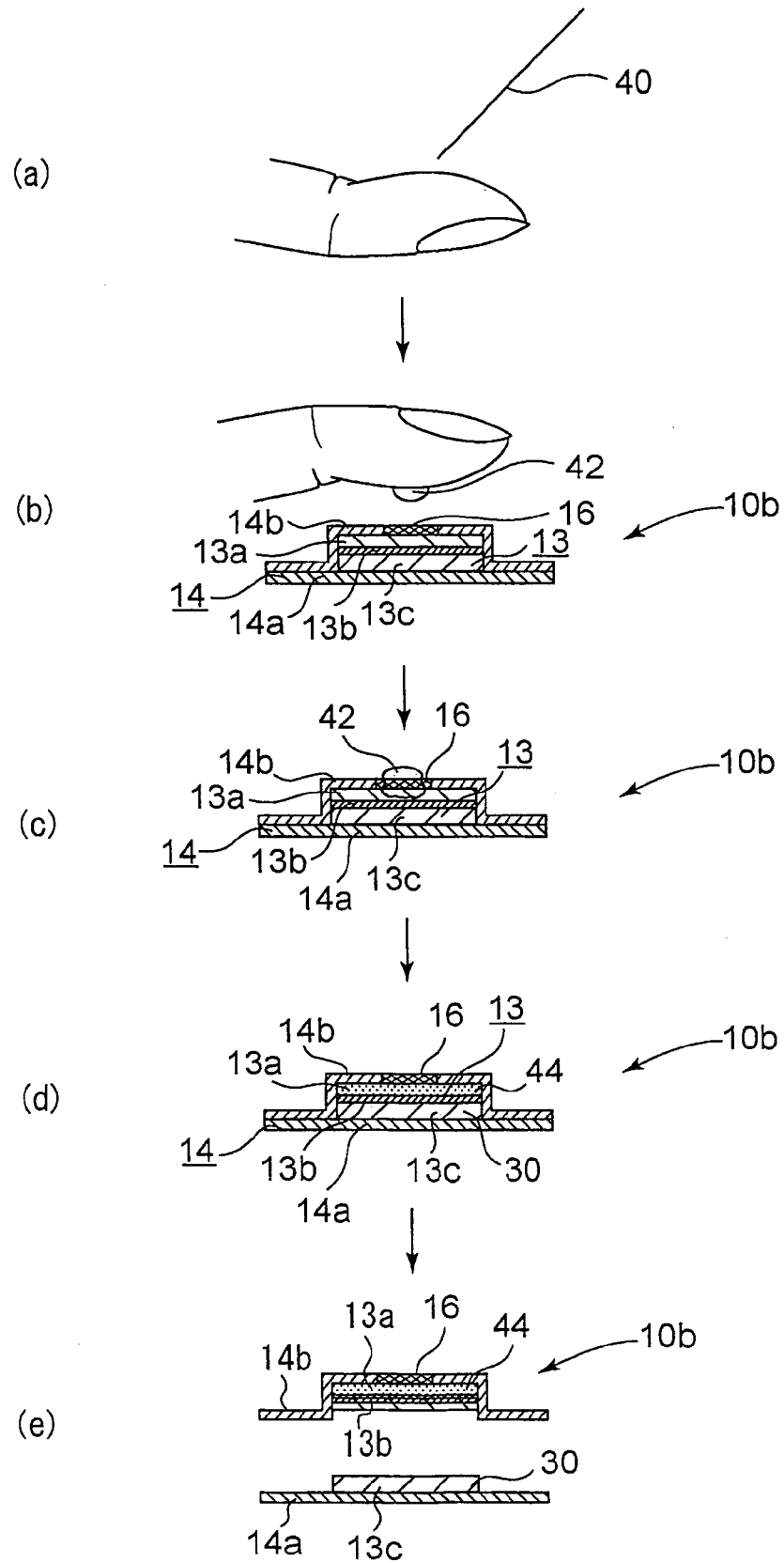
FIG. 13, consisting of FIGS. 13(a) to 13(e), is a descriptive schematic view showing one example of a process sequence according to a third aspect of a plasma or serum sampling method of the present invention.

FIG. 12 is a flowchart showing one example of a process sequence according to a third aspect of a plasma or serum sampling method of the present invention using the fifth embodiment (the third aspect) (FIG. 11) of a plasma or serum separator of the present invention. FIG. 13 is a descriptive schematic view showing each step of FIG. 12. The steps 200 to 205 of FIG. 12 and the parts (a) to (d) are similar to the steps 200 to 205 of FIG. 9 and the parts (a) to (d), and the plasma or serum 30 is absorbed in the plasma or serum absorbing member (third layer). The third layer 13c having absorbed the plasma or serum 30 is disassembled and exposed to the outside air to desiccate the plasma or serum 30 (step 207 in FIG. 12 and FIG. 13(e)). More, in the step 207, the third layer 13c having absorbed the plasma or serum 30 is exposed to the outside air to desiccate the plasma or serum 30, and after that the third layer 13c may be disassembled. The desiccated plasma or serum 30 is sent by mail or the like means to an examination site where a necessary examination can be carried out (step 210 in FIG. 12).

Figure 14:
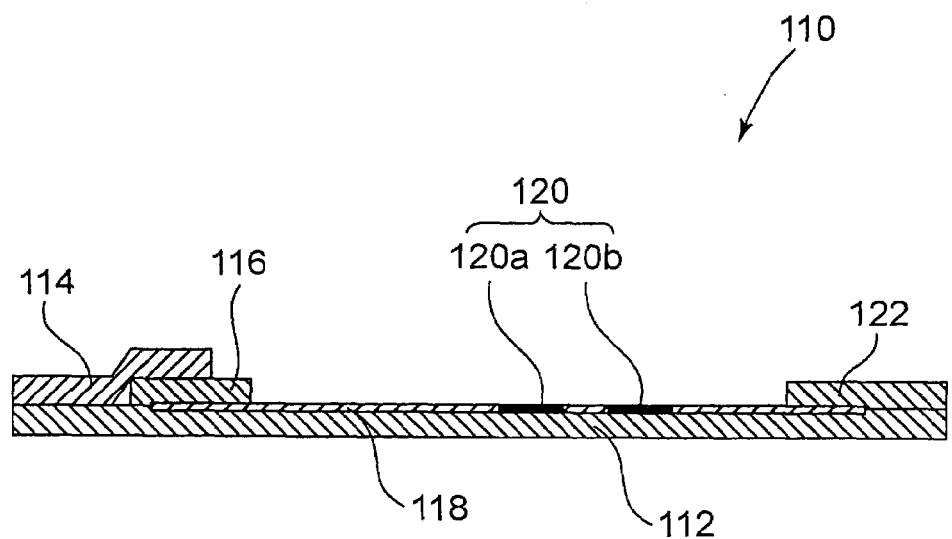
FIG. 14 is one example of a design view of a test carrier of the present invention.

FIG. 14 is a sectional view showing one embodiment of a test carrier of the present invention, wherein there is shown a case where a strip used in an immunochromatography is used as a test carrier and the fourth aspect of a plasma or serum separator of the present invention is used as a sample pad.

In the figure, reference numeral 110 designates a test carrier, which has a long support plate 112 made of plastic materials or the like. A plasma or serum separation layer 114 is provided on the upper surface of one end portion of the support plate 112. As the plasma or serum separation layer 114, there may be also used a blood separation member containing fibrous materials and/or porous materials coated with one kind or two or more kinds selected from the group consisting of hexylene glycol, propanol with a butoxy group and acrylamide with a butoxy group, which is described in the first aspect of a plasma or serum separator of the present invention. It is especially preferable to use a blood separation member not only having a red blood aggregating function, but also containing glass fibers coated with at least on kind selected from the group consisting of hexylene glycol, propanol with a butoxy group and acrylamide with a butoxy group. Using the blood separation member, hemolysis can be suppressed to a practically non-problematical level in the course of separation, separation of plasma or serum from blood cells starts at the same time as dropping of blood and hence quick separation can be realized without a delay time in which whole blood is developed in the fibrous materials and/or porous materials.

Reference numeral 116 designates a conjugate pad made of glass fibers or the like and the distal end portion of the plasma or serum separation member 114 is provided adjacent to the conjugate pad 116 so as to cover the proximal end portion of the conjugate pad 116 provided on the support plate 112. The conjugate pad 116 contains an antibody or an antigen labeled with latex, gold colloid or the like.

Reference numeral 118 designates a development layer serving as a test region and made of a nitrocellulose film or the like. The development layer 118 is provided in the central portion of the upper surface of the support plate 112 and constituted of a solid phase band 120 such as a capture zone 120a and a control zone 120b. The solid band 120 contains an antibody and an antigen. Reference numeral 122 designates a water-absorbing layer made of glass fibers or the like provided on the upper surface of the other end portion of the support plate 112, which works so as to cause non-reacted materials having not reacted in the solid phase band 120 to migrate to outside of the solid band 120 by a water-absorbing function.

Description will be given of the function of the test carrier 110 bellow. When a blood sample component and a reaction solution are dropped onto the plasma or serum separation layer 114, red blood cells in the blood sample component are held by glass fibers in the plasma or serum separation layer 114 to thereby isolate plasma or serum.

The isolated plasma or serum component and the reaction solution cause an antigen-antibody reaction with an antibody or an antigen labeled with latex, gold colloid or the like in the conjugate pad 116 and a reaction product and a non-reacted substance migrate in a lateral direction, that is to the development layer 118.

The reaction product causes an antigen-antibody reaction with an antibody or an antigen in the solid band 120 of the development layer 118 to produce a measurement composite colored with the labeling substance. A shade of coloring matter based on an amount of the labeling substance in the measurement composite in the solid phase band 120 is visually expressed or a shade of a color of the solid band 120 is expressed using an intensity of coloring matter absorption light, thereby measurement on a analysis target in a blood sample component being realized.

Alternatively, latex itself is colored with a material having a property of fluorescence or other light emission and an amount of the labeling substance in a solid band is obtained from an intensity of the fluorescence or other light emission, which is expressed as a qualitative amount or a quantitative amount.

Further, a non-reacted material having not reacted in the solid band 120 of the development layer 118 is migrated outside of the solid band 120 of the development layer 118 by the action of the water-absorbing layer 122.

Figure 15:
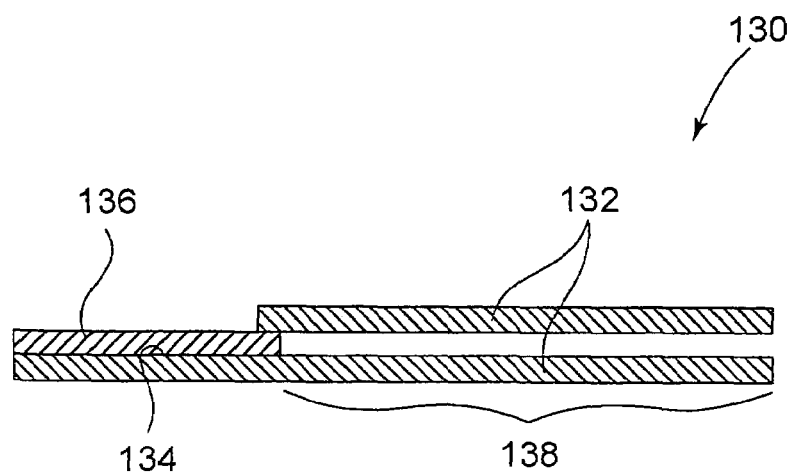
FIG. 15 is another example of the design view of a test carrier of the present invention.

FIG. 15 is a sectional view showing another embodiment of a test carrier of the present invention, in which there is shown an example of a test carrier in a case where after plasma or serum is isolated from whole blood, the plasma or serum is taken into a capillary tube and then using the transparent capillary tube bilirubin in the plasma or serum with an absorption wavelength of 455 nm is directly subjected to colorimetry.

In the figure, reference numeral 130 designates a test carrier having a long capillary tube 132 made of glass, transparent plastics or the like. A mounting portion 134 is formed at one end portion of the capillary tube 132 by removing a part of the capillary tube 132.

A plasma or serum separation layer 136 is provided on the mounting portion 134. The plasma or serum separation layer 136 is made of a blood separation member similar to the plasma or serum separation layer 114 of FIG. 14. A portion of the capillary tube 132 other than a portion where the plasma or serum separation layer 136 is provided, works as the test region 138 as shown in FIG. 15.

With the construction described above, a blood sample component is dropped onto the plasma or serum separation layer 136 and thereby, red blood cells in the blood sample component are held by glass fibers in the plasma or serum separation layer 136 and the plasma or serum is isolated from red blood cells.

The isolated plasma or serum is taken into the test region 138 by the action of a capillary force of the capillary tube 132, light is irradiated from the upper surface or bottom surface of the capillary tube 132, and the irradiated light is detected at the bottom surface or upper surface thereof, a bilirubin concentration with an absorbance at a wavelength of 455 nm being measured.

Description will be given of the present invention showing examples bellow.

FABRICATION EXAMPLE 1

In Examples 1 and 2 described later, a plasma or serum separator similar to that shown in FIG. 3 was fabricated in a way described below and used.

A glass fiber filter paper GF/D (manufactured by Whatman Inc. with a thickness of 0.2 mm, and an average pore size of 5.7 μm) cut into a size of 10 mm in width and 20 mm in length was immersed in a 0.05% aqueous solution of N-butoxymethyl acrylamide (manufactured by Wako Pure Chemical Industries Ltd.) and thereafter, the glass fiber filter cut was desiccated at a temperature of 70° C. for 30 min to thus prepare a blood separation member.

A polypropylene plastic film (with a thickness of 100 μm) on which a pressure sensitive adhesive was applied was used as a holding member. Both surfaces of the blood separation member were, as shown in FIG. 3(b), adhered with a base film (with a size of 20 mm ×30 mm) and a covering film (with a size of 20 mm ×15 mm), respectively, leaving a size of 10 mm ×10 mm as a blood introducing portion. Thereafter, as shown in FIG. 3(a), a distal end portion of the covering film was perforated with a syringe needle (22G diameter) to form a plasma or serum sampling aperture, and thus a plasma or serum separator was fabricated. That is, the fabricated square plasma or serum separator was 10 mm ×20 mm square having a blood separation member covered With a plastic film, which includes a blood introducing portion with an opening of 10 mm ×10 mm square at one end portion of the upper surface thereof and a plasma or serum sampling aperture with 22G diameter at another distal end portion of the side surface thereof.

EXAMPLE 1

Using the plasma or serum separator of the present invention obtained in Fabrication Example 1, plasma or serum was sampled to measure a total bilirubin amount in the plasma or serum.

Figure 6:
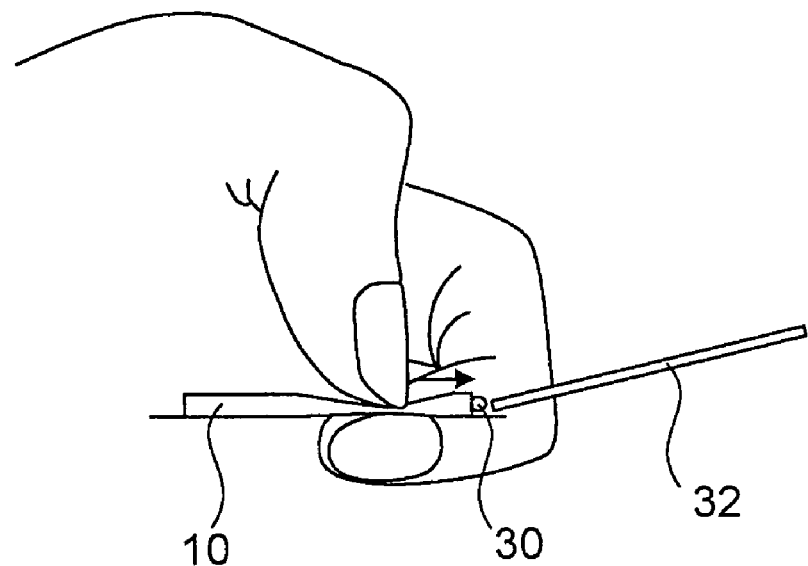
FIG. 6 is a descriptive schematic view showing one embodiment of a process for taking out plasma or serum in a first aspect of a plasma or serum sampling method of the present invention.
Figure 7:
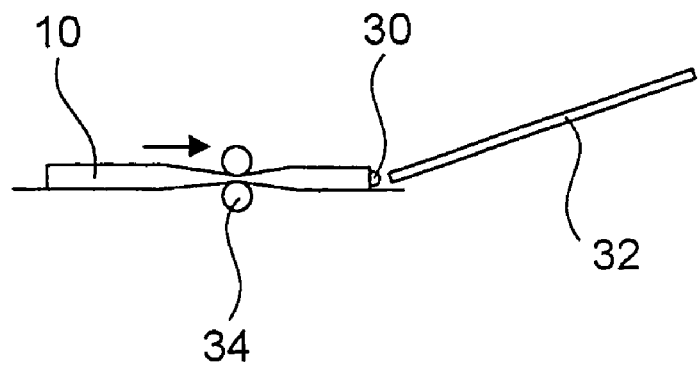
FIG. 7 is a descriptive schematic view showing another embodiment of a process for taking out plasma or serum in a first aspect of a plasma or serum sampling method of the present invention.

A total of ten kinds of whole blood test samples having different concentrations of bilirubin in blood (Test Sample Nos. 1 to 10, in which heparin was used as an anticoagulant) were prepared and 50 μL of a blood sample was dropped onto the blood introducing portion of the plasma or serum separator and after a lapse of 120 sec, the plasma or serum isolated on the blood separation member was, as shown in FIG. 6, squeezed out from between the plastic films to the side of the plasma or serum sampling aperture located on the side surface of the distal end portion by a nail. The plasma or serum was sampled in a capillary tube (with a trade name of CAPILLARY TUBES manufactured by Drummond Scientific Co.) by the action of a capillary phenomenon.

The capillary tube containing the sampled plasma or serum was set in Photo BH meter-V (a total bilirubin analyzer manufactured by Sanko Junyaku Co., Ltd.), shown in FIG. 17, to measure a total bilirubin value in the plasma or serum, the measuring results being shown in Table 1.

COMPARATIVE EXAMPLE 1

The same blood samples as those in Example 1 (Test Sample Nos. 1 to 10) were sampled in capillary tubes by about 50 μL each. The capillary tubes were loaded in a centrifuge for exclusive capillary tube use (with a trade name of Labocrit BH-2000 manufactured by Kokusan Corporation and distributed by Sanko Junyaku Co., Ltd.), then centrifugal separation was conducted for 5 min at 12000 rpm to isolate plasma or serum and thereafter a total bilirubin value in the plasma or serum was measured in a procedure similar to that in Example 1, the measuring results being shown in Table 1.

TABLE 1

| | Test Sample Nos. | | | | | | | | | mg/dL |
|---|---|---|---|---|---|---|---|---|---|---|
| | 1 | 2 | 3 | 4 | 5 | 6 | 7 | 8 | 9 | 10 |
| Example 1 | 0.7 | 3.9 | 2.3 | 1.6 | 12.1 | 7.2 | 8.8 | 10.4 | 5.5 | 13.9 |
| Comparative Example 1 | 0.8 | 4.0 | 2.4 | 1.7 | 11.9 | 7.1 | 8.7 | 10.2 | 5.5 | 13.9 |

Figure 16:
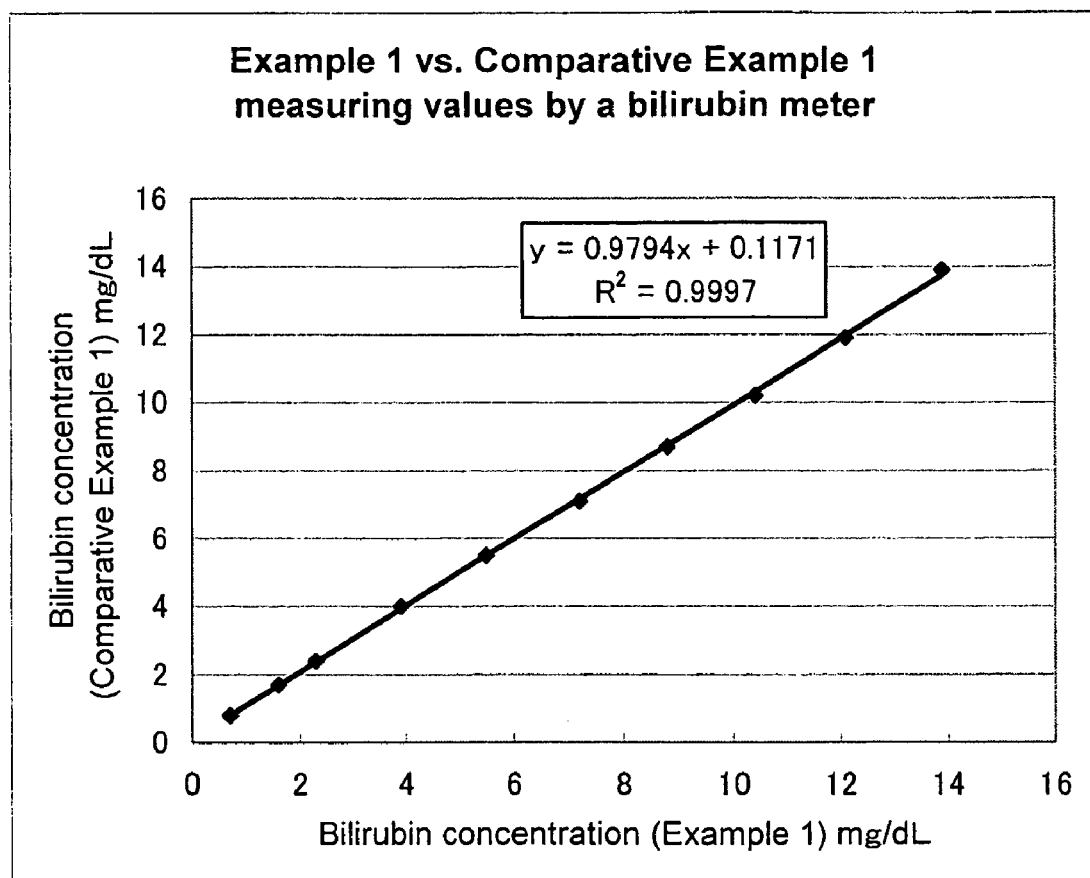
FIG. 16 is a graph showing results of measurement on bilirubin concentration in Example 1 and Comparative Example 1.

FIG. 16 is a graph obtained by plotting the measuring results in Comparative Example 1 against those in Example 1 with respect to each test sample. The correlation between both is good as shown in FIG. 16. As clear from the results in Table 1 and FIG. 16, in each test sample there is no difference between total bilirubin values obtained with a plasma or serum separator of the present invention and obtained by isolating with a conventional centrifuge.

EXAMPLE 2

Using the plasma or serum separator of the present invention fabricated in Fabrication Example 1, plasma or serum was sampled from blood and then ALT (alanine aminotransferase) in the plasma or serum was measured.

Three kinds of blood (Test Sample Nos. 11 to 13 in which EDTA was used as an anticoagulant) were prepared and 50 μL of a blood test sample was dropped onto the blood introducing portion of the plasma or serum separator and after a lapse of 120 sec, the plasma or serum isolated on the blood separation member was squeezed out from between the plastic films to the side of the plasma or serum sampling aperture located on the side surface of the distal end portion by a nail. Ten μL of the plasma or serum was sampled with a quantitative pipet and ALT (alanine aminotransferase) is measured using an ALT reagent (with a trade name of Santest L-ALT manufactured by Katayama Chemical Industries Co., Ltd.) as a biochemical examination with a spectrophotometer (with a trade name of UV-730 manufactured by Shimadzu Corporation), the measuring results being shown in Table 2.

COMPARATIVE EXAMPLE 2

The same blood samples as those in Example 2 (Test Sample Nos. 11 to 13) were prepared by about 5 mL each and centrifugal separation was conducted using the conventional centrifugal separation method for 10 min at 3000 rpm to sample 10 μL of supernatant plasma or serum and ALT in the plasma or serum was measured in the same procedure as that in Example 1, the measuring results being shown in Table 2.

TABLE 2

| Test Sample No. | Example 2 | Comparative Example 2 | U/mL |
|---|---|---|---|
| 11 | 4.5 | 4.5 | |
| 12 | 4.5 | 4.5 | |
| 13 | 23.5 | 23.6 | |

As clear from the results in Table 2, no difference was observed between ALT amounts in the same test samples in Example 2 and Comparative Example 2.

EXAMPLE 3

A plasma or serum separator having a plasma or serum laminate similar to that shown in FIG. 8 (wherein the network member 20 is omitted) was fabricated as described below.

First layer (a plasma or serum separation member): similar to the plasma or serum separation member in Fabrication Example 1.

Second layer (a hemolysis blocking member): nitrocellulose (with a pore diameter of 0.45 μm)

Third layer (a plasma or serum absorbing member): a glass fiber filter paper GF/D (manufactured by Whatman Inc. with a thickness of 0.2 mm and an average pore size of 5.7 μm)

Holding member: similar to that in Fabrication Example 1

Blood introducing portion: fabricated in a similar manner to that in Fabrication Example 1

Plasma or serum sampling aperture: fabricated in a similar manner to that in Fabrication Example 1

Using the plasma or serum separator fabricated as described above and whole blood test samples similar to those in Example 1, plasma or serum was sampled in a procedure similar to that in FIG. 10 and thereafter, a bilirubin value was measured. Thereby, it was possible to obtain the measuring results similar to those in Example 1.

FABRICATION EXAMPLE 2

A glass fiber filter paper GF/D (manufactured by Whatman Inc. with a thickness of 0.675 μm and an average pore size of 5.7 μm) cut into a size of 4 mm in width and 15 mm in length was immersed in a 0.05% aqueous solution of N-butoxymethyl acrylamide (manufactured by Wako Pure Chemical Industries Ltd.) and thereafter, the glass fiber filter cut was desiccated at a temperature of 70° C. for 30 min to thus prepare a blood separation pad (that is, a plasma or serum separation member).

FABRICATION EXAMPLE 3

A glass fiber filter paper GF/D (manufactured by Whatman Inc. with a thickness of 0.675 μm and an average pore size of 5.7 μm) cut into a size of 4 mm in width and 15 mm in length was immersed in a 0.05% aqueous solution of 1-butoxy-2-propanol (manufactured by Wako Pure Chemical Industries Ltd.) and thereafter, the glass fiber filter cut was desiccated at a temperature of 70° C. for 30 min to thus prepare a blood separation pad.

FABRICATION EXAMPLE 4

A glass fiber filter paper GF/D (manufactured by Whatman Inc. with a thickness of 0.675 μm and an average pore size of 5.7 μm) cut into a size of 4 mm in width and 15 mm in length was immersed in a 0.05% aqueous solution of hexylene glycol (2-methyl-2, 4-pentanediol, manufactured by Tokyo Kasei Kogyo Co., Ltd.) and thereafter, the glass fiber filter cut was desiccated at a temperature of 70° C. for 30 min to thus prepare a blood separation pad.

EXAMPLE 4 TO 6

Plasma or Serum Separation Property: a plasma or serum separation ability and a hemoglobin value in isolated plasma or serum were measured on the glass fiber plasma or serum separation pads of the present invention fabricated in Fabrication Examples 2 to 4 (Example 4; glass fibers containing 0.5% N-butoxymethyl acrylamide, Example 5; glass fibers containing 0.5% 1-butoxy-2-propanol, Example 6; glass fibers containing 0.5% hexylene glycol).

Measuring Method of Plasma or Serum Separation Ability: 80 μL of blood having hematocrit 56% was dropped at each end of the above plasma or serum separation pads each of a size of 4 mm in width and 15 mm in length to measure an area ratio between an area of a blood cell portion and an area of a plasma or serum portion isolated on each plasma or serum separation pad, the measuring results being shown in Table 3.

Measurement of Separation Time: a blood sample component was dropped onto each plasma or serum separation pad to visually measure a time required till red blood cells migrate and stop in the pad. The measuring results are shown in Table 3.

Measurement of a Hemoglobin Value: 150 μL of blood having hematocrit 56% is dropped onto each plasma or serum separation pad having a size of 4 mm in width and 15 mm in length using a pipet and a capillary tube is brought into contact with plasma or serum isolated on each plasma or serum separation pad to sample plasma or serum. An absorbance of a sampled plasma or serum was measured at a wavelength of 575 μm using Photo BH meter-V (manufactured by Sanko Junyaku Co., Ltd.) and a hemoglobin concentration was calculated from an absorbance with 15.1 g/dl of Hemoglobin Control (Hemocon-N) (manufactured by Azwell Inc.) as a reference, the measuring results being shown in Table 3.

COMPARATIVE EXAMPLE 3 TO 7

Glass fiber plasma or serum separation pads were fabricated in a way similar to that in Example 4 using a glass fiber filter paper GF/D (manufactured by Whatman Inc.) (Comparative Example 3), glass fibers containing 1% mannitol and 0.1% albumin (Comparative Example 4), glass fibers containing 2% polyvinyl alcohol (Comparative Example 5), glass fibers containing polybrene (Comparative Example 6) and glass fibers containing 2% polyvinyl alcohol and polybrene (Comparative Example 7) to measure their plasma or serum separation properties, plasma or serum separation ability and hemoglobin amounts in a procedure similar to that in Example 4, the measuring results being shown in Table 3 together with the results of Examples 4 to 6.

TABLE 3

|  | Plasma or serum separation pads | Area Ratios | Separation Times | Hemoglobin Values |
|---|---|---|---|---|
| Example 4 | Glass fibers containing 0.5% N-butoxymethyl acrylamide | 28% | 50 sec | <10 mg/dL |
| Example 5 | Glass fibers containing 0.5% 1-butoxy-2-propanol | 28% | 50 sec | <10 mg/dL |

TABLE 3-continued

| | Plasma or serum separation pads | Area Ratios | Separation Times | Hemoglobin Values |
|---|---|---|---|---|
| Example 6 | Glass fibers containing 0.5% hexylene glycol | 32% | 50 sec | <10 mg/dL |
| Comparative Example 3 | Glass fiber filter paper GF/D (manufactured by Whatman Inc.) | <20% | 150 sec | 300 mg/dL< |
| Comparative Example 4 | Glass fibers containing 1% mannitol and 0.1% albumin | 28% | 300 sec | 788 mg/dL |
| Comparative Example 5 | Glass fibers containing 2% polyvinyl alcohol | <5% | 120 sec | 1000 mg/dL< |
| Comparative Example 6 | Glass fibers containing polybrene | 20% | 100 sec | 110 mg/dL |
| Comparative Example 7 | Glass fibers containing 2% polyvinyl alcohol and polybrene | 26% | 120 sec | 330 mg/dL |

As clear from the results in Table 3, it was found that the plasma or serum separation pads (Examples 4 to 6) had properties that not only a red blood cell separation ability and hemolysis were lower but also a separation time of plasma or serum was shorter as compared with those of the conventional plasma or serum separation pads (Comparative Examples 3 to 7).

While in the Examples 4 to 6, there were shown cases where 0.5% hexylene glycol, 0.5% N-butoxymethyl acrylamide and 0.5% 1-butoxy-2-propanol were independently incorporated in glass fibers, it was confirmed that the results similar to those in Examples 4 to 6 were obtained in cases where they were mixed at the same ratio.

CAPABILITY OF EXPLOITATION IN INDUSTRY

As described above, according to the first to third aspects of the plasma or serum separator of the present invention, without using a centrifuge or a special device and a tool for pressuring or reducing a pressure as in the prior art, an arbitrarily predetermined amount of plasma or serum can be isolated and collected in a liquid or dry state from a very small, indefinite amount of a whole blood sample easily and quickly without leakage and hemolysis of a blood cell component. According to the plasma or serum sampling method of the present invention, since plasma or serum can be isolated and collected from a very small amount of whole blood, it is only required to sample blood by sticking a needle into a finger tip or the like of a person to be examined without using a syringe in obtaining a blood test sample; therefore it is possible to reduce a burden imposed on a person to be examined and also to sample blood personally by a person to be examined. Furthermore, using the sampling method of the present invention, a blood test can be performed instantly at any time; it is useful in an emergency test and home-use test. Especially according to the plasma or serum sampling method of the present invention, in measurement on a bilirubin concentration in blood, which is a kernicterus examination for a neonate, blood obtained by sticking a needle in a sole of a neonate is used for sampling plasma or serum into a capillary tube using one of the first to third aspect of the plasma or serum separator of the present invention to instantly enable a bilirubin concentration to be measured using a bilirubin analyzer for exclusive capillary tube use; the method is capable of coping with measurement in hospital, a visiting examination in home after leaving hospital and home-use test at any time.

According to the fourth aspect of the plasma or serum separator of the present invention, a great effect is achieved that when isolating plasma or serum from whole blood, not only is isolation of red blood cells quickly effected, but also isolation ability is high, and less of hemolysis is realized.

According to the plasma or serum separation method of the present invention, plasma or serum can be quickly isolated from whole blood under suppression of hemolysis without using a centrifuge. According to the test carrier of the present invention, even in a point of care examination in a clinical laboratory test, plasma or serum can be isolated from whole blood substantially without causing hemolysis. According to glass fibers of the present invention, a cell component of non-diluted whole blood can be very well separated from plasma or serum while suppressing hemolysis.

The invention claimed is:

1. A plasma or serum separator for isolating plasma or serum from whole blood, said separator comprising:
   a blood separation member,
   a holding member covering and holding the blood separation member;
   a blood introducing portion formed in a portion of the holding member covering a proximal end portion of the blood separation member; and
   a plasma or serum sampling aperture formed in a portion of the holding member covering a distal end portion of the blood separation member,
   wherein the whole blood is introduced into the blood separation member through the blood introducing portion, and the introduced whole blood is separated such that the plasma or serum is located in the distal end portion of the blood separation member, while blood cells are located in the proximal end portion of the blood separation member; thereby enabling the plasma or serum located in the distal end portion of the blood separation member to be sampled through the plasma or serum sampling aperture,
   wherein the blood separation member is made of a fibrous material and/or a porous material, and
   wherein the fibrous material and/or the porous material (A) is one kind or two or more kinds selected from the group consisting of glass fibers, non-woven fabrics, cellulose fibers, polyester, polypropylene, polyamide, polyethylene, polyurethane and polyvinyl formal, and (B) is coated with propanol with a butoxy group and/or acrylamide with a butoxy group.

2. The plasma or serum separator according to claim 1, wherein the fibrous material is glass fibers.

3. The plasma or serum separator according to claim 1, wherein the propanol with butoxy is butoxypropanol.

4. The plasma or serum separator according to claim 1, wherein the acrylamide with a butoxy group is butoxymethylacrylamide.

5. The plasma or serum separator according to claim 1, wherein the holding member is a transparent or semi-transparent liquid non-penetrable film.

6. The plasma or serum separator according to claim 1, wherein the blood introducing portion is covered with a network member capable of being penetrated by blood.

7. A plasma or serum sampling method employing a plasma or serum separator according to claim 1, said method comprising the steps of:
sticking a needle-like tool in a blood sampling portion to cause the portion to bleed;
bringing the blood introducing portion of the plasma or serum separator into contact with the bleeding site to introduce whole blood into the blood separation member;
subjecting the introduced whole blood to separation by the blood separation member such that the plasma or serum is located in the distal end portion thereof, while blood cells are located in the proximal end portion thereof; and
sampling plasma or serum staying in the distal end portion of the blood separation member through the plasma or serum sampling aperture.

8. The plasma or serum sampling method according to claim 7, wherein the fibrous material is glass fibers.

9. The plasma or serum sampling method according to claim 7, wherein the propanol with a butoxy group is butoxypropanol.

10. The plasma or serum sampling method according to claim 7, wherein the acrylamide with a butoxy group is butoxymethylacrylamide.

11. The plasma or serum sampling method according to claim 7, wherein the holding member is a transparent or semi-transparent liquid non-penetrable film.

12. The plasma or serum sampling method according to claim 7, wherein the blood introducing portion is covered with a network member capable of being penetrated by blood.

13. A plasma or serum separator for isolating plasma or serum from whole blood, said separator comprising a blood separation member having a fibrous material and/or a porous material coated with propanol with a butoxy group and/or acrylamide with a butoxy group.

14. The plasma or serum separator according to claim 13, wherein the propanol with a butoxy group is butoxypropanol.

15. The plasma or serum separator according to claim 13, wherein the acrylamide with a butoxy group is butoxymethylacrylamide.

16. The plasma or serum separator according to claim 13, wherein the fibrous material and/or the porous material is one kind or two or more kinds selected from the group consisting of glass fibers, non-woven fabrics, cellulose fibers, polyester, polypropylene, polyamide, polyethylene, polyurethane and polyvinyl formal.

17. The plasma or serum separator according to claim 13, wherein plasma or serum is isolated from whole blood by bringing the whole blood into contact with the blood separation member to hold red blood cells in the blood separation member and hemolysis is suppressed by using the blood separation member.

18. A plasma or serum separating method of isolating plasma or serum from whole blood by bringing the whole blood into contact with the blood separation member to hold red blood cells in the blood separation member, wherein hemolysis is suppressed by using a plasma or serum separator according to claim 13.

19. A test carrier comprising: a plasma or serum separation layer for isolating plasma or serum from a blood sample component and a test region for testing the isolated plasma or serum, wherein the plasma or serum separation layer comprises a plasma or serum separator according to claim 13 to thereby suppress hemolysis.

20. A plasma or serum separator for isolating plasma or serum from whole blood, said separator comprising:
a blood separation member,
a holding member covering and holding the blood separation member;
a blood introducing portion formed in a portion of the holding member covering a proximal end portion of the blood separation member; and
a plasma or serum sampling aperture formed in a portion of the holding member covering a distal end portion of the blood separation member,
wherein the whole blood is introduced into the blood separation member through the blood introducing portion, and the introduced whole blood is separated such that the plasma or serum is located in the distal end portion of the blood separation member, while blood cells are located in the proximal end portion of the blood separation member; thereby enabling the plasma or serum located in the distal end portion of the blood separation member to be sampled through the plasma or serum sampling aperture,
wherein the blood separation member is made of a fibrous material, and
wherein the fibrous material is glass fibers and coated with hexylene glycol.

21. A plasma or serum sampling method employing a plasma or serum separator according to claim 20, said method comprising the steps of:
sticking a needle-like tool in a blood sampling portion to cause the portion to bleed;
bringing the blood introducing portion of the plasma or serum separator into contact with the bleeding site to introduce whole blood into the blood separation member;
subjecting the introduced whole blood to separation by the blood separation member such that the plasma or serum is located in the distal end portion thereof, while blood cells are located in the proximal end portion thereof; and
sampling plasma or serum staying in the distal end portion of the blood separation member through the plasma or serum sampling aperture.

22. The plasma or serum separator according to claim 20, wherein the holding member is a transparent or semi-transparent liquid non-penetrable film.

23. The plasma or serum separator according to claim 20, wherein the blood introducing portion is covered with a network member capable of being penetrated by blood.

24. The plasma or serum sampling method according to claim 21, wherein the holding member is a transparent or semi-transparent liquid non-penetrable film.

25. The plasma or serum sampling method according to claim 21, wherein the blood introducing portion is covered with a network member capable of being penetrated by blood.

26. A test carrier comprising:
a plasma or serum separation layer for isolating plasma or serum from a blood sample component and a test region for testing the isolated plasma or serum, wherein the plasma or serum separation layer comprises a plasma or serum separator,
wherein said separator includes a blood separation member having a fibrous material coated with hexylene glycol, wherein the fibrous material is glass fibers, and wherein said separator suppresses hemolysis.

* * * * *